(12) United States Patent
Warthoe

(10) Patent No.: US 10,100,353 B2
(45) Date of Patent: Oct. 16, 2018

(54) TECHNIQUE COMBINING PCR AND LOOP-MEDIATED ISOTHERMAL AMPLIFICATION FOR THE DETECTION OF NUCLEIC ACIDS

(71) Applicant: Peter Warthoe, Copenhagen Ø (DK)

(72) Inventor: Peter Warthoe, Copenhagen Ø (DK)

(73) Assignee: Peter Warthoe, Copenhagen (DK)

( * ) Notice: Subject to any disclaimer, the term of this patent is extended or adjusted under 35 U.S.C. 154(b) by 539 days.

(21) Appl. No.: 14/400,717

(22) PCT Filed: May 13, 2013

(86) PCT No.: PCT/EP2013/059767
§ 371 (c)(1),
(2) Date: Nov. 12, 2014

(87) PCT Pub. No.: WO2013/171140
PCT Pub. Date: Nov. 21, 2013

(65) Prior Publication Data
US 2015/0126382 A1 May 7, 2015

(30) Foreign Application Priority Data

May 14, 2012 (DK) .................................. 2012 00339
Oct. 5, 2012 (EP) ...................................... 12187507

(51) Int. Cl.
| | | |
|---|---|---|
| C12Q 1/68 | (2018.01) | |
| C12Q 1/686 | (2018.01) | |
| C12Q 1/6853 | (2018.01) | |
| C12Q 1/689 | (2018.01) | |
| C12Q 1/6895 | (2018.01) | |

(52) U.S. Cl.
CPC ............ *C12Q 1/686* (2013.01); *C12Q 1/689* (2013.01); *C12Q 1/6853* (2013.01); *C12Q 1/6895* (2013.01); *C12Q 2525/301* (2013.01); *C12Q 2531/119* (2013.01); *C12Q 2600/16* (2013.01)

(58) Field of Classification Search
None
See application file for complete search history.

(56) References Cited

U.S. PATENT DOCUMENTS 5,491,225 A * 2/1996 Picone ................. C07K 14/195
435/6.15

FOREIGN PATENT DOCUMENTS

| CN | 101173317 | 5/2008 |
|---|---|---|
| CN | 101348835 | 1/2009 |
| WO | 2009049630 | 4/2009 |

OTHER PUBLICATIONS

Matsuzawa et al. Japanese Journal of Medical Mycology 2010; 51: 109-116.*
Abdin et al. Archives of Microbiology 2010; 192: 409-425.*
Mori et al. Journal of Infection and Chemotherapy 2009; 15: 62-69.*
Shao et al. International Journal of Food Microbiology 2011; 148: 75-79. (Year: 2011).*
Notomi T et al: "Loop-mediated isothermal amplification of DNA", Nucleic Acids Research, Oxford University Press, Surrey, GB, vol. 28, No. 12, Jan. 1, 2000 (Jan. 1, 2000), pp. 1-7, XP002481306, ISSN: 0305-1048, DOI: 10.1093/NAR/28.12.E63 cited in the application.
Tomita Norihiro et al: "Loop-mediated isothermal amplification (LAMP) of gene sequences and simple visual detection of products", Nature Protocols, Nature Publishing Group, GB, vol. 3, No. 5, May 1, 2008 (May 1, 2008), pp. 877-882, XP008103938, ISSN: 1750-2799, DOI: 10.1038/NPROT.2008.57 [retrieved on Apr. 24, 2008].
Hanaki K-I et al.: "Loop-mediated isothermal amplification assays for identification of antiseptic- and methicillin-resistant *Staphylococcus aureus*", Journal of Microbiological Methods, vol. 84, 2011, pp. 251-254, XP002693137.
Misawa Y et al.: "Application of loop-mediated isothermal amplification technique to rapid and direct detection of methicillin-resistant *Staphylococcus aureus* (MRSA) in blood cultures.", Journal of Infection and Chemotherapy, vol. 13, 2007, pp. 134-140, XP002693138.

* cited by examiner

*Primary Examiner* — Angela M. Bertagna
(74) *Attorney, Agent, or Firm* — Duane Morris LLP; Gregory M. Lefkowitz; Jason M. Nolan

(57) ABSTRACT

The present invention relates to a method and a kit of parts for detecting the presence or absence of one or more target nucleic acid sequences in a sample, the method comprising a sequence of steps for pre-amplifying the sample by means of a polymerase chain reaction, followed by a sequence of steps comprising an isothermal amplification of the pre-amplified sample, wherein the isothermal amplification comprises a pair of primers comprising a forward primer having a 3' part that is substantially complementary to a first part of the target sequence, the presence or absence of which is to be detected, and a 5' part that is substantially homolog to a second part of the target sequence, and a reverse primer comprising a 3' part that is substantially homolog to a fourth part of the target sequence and a 5' part that is substantially complementary to a third part of the target sequence.

13 Claims, 2 Drawing Sheets
Specification includes a Sequence Listing.

TECHNIQUE COMBINING PCR AND LOOP-MEDIATED ISOTHERMAL AMPLIFICATION FOR THE DETECTION OF NUCLEIC ACIDS

CROSS-REFERENCE TO RELATED APPLICATIONS

This application is a § 371 national stage entry of International Application No. PCT/EP2013/059767, filed May 13, 2013, which claims priority to Danish Patent Application No. PA 2012 00339, filed May 14, 2012, and European Patent Application No. 12187507.4, filed Oct. 5, 2012, the entire contents of which are incorporated herein by reference.

TECHNICAL FIELD

The present invention relates to a method for detecting the presence or absence of one or more target nucleic acid sequences in a sample. Further, the invention relates to a kit of parts suitable for detecting the presence or absence of one or more target nucleic acid sequences in a sample.

BACKGROUND

Detection of the presence or absence of particular nucleic acid sequences in samples by use of nucleic acid amplification techniques has proven a powerful diagnostic tool with a multitude of applications.

The introduction of the polymerase chain reaction (PCR) provided the possibility for a rapid and specific amplification of specific target nucleic acid sequences present in samples. The PCR technique thereby provided a significant diagnostic tool for the detection of nucleic acid sequences in samples, and the introduction of this technique opened a new field of diagnostic applications.

Today, the polymerase chain reaction is well known to the skilled person.

However, it has proven to be difficult to detect the presence or absence of multiplex target nucleic acid sequences present in low copy numbers in a sample. Detecting several target sequences by parallel simplex PCR, each with a single primer set specific for the pathogen, are often not feasible due to a limited quantity of target DNA in the starting material. Alternatively, multiplex PCR using multiplex primer sets in the same reaction may be limited in detection sensitivity due to the inherent variability of amplification efficiencies of the different primer sets. Further, the PCR technique has proven to be time-consuming and difficult to handle in practice in a number of applications due to the requirement of a multitude of repeating cycles of thermal cycling (cycles of temperature shifts where different steps in the PCR process are taking place). The requirement of thermal cycling also causes problems in the manufacture of suitable detection devices where the requirements for rapid cooling and heating result in technical design problems for the device manufacturer. In order to provide a simpler device, an isothermal amplification technique would be more suitable.

To circumvent this and other difficulties, a number of alternative methods for the amplification of nucleic acid sequences have been developed, e.g. isothermal techniques such as transcription mediated amplification (TMA) or self-sustained sequence replication (3SR), nucleic acid sequence-based amplification (NASBA), signal-mediated amplification of RNA technology (SMART), strand displacement amplification (SDA), rolling circle amplification (RCA), loop-mediated isothermal amplification of DNA (LAMP), isothermal multiple displacement amplification (IMDA), helicase-dependent amplification (HDA), single primer isothermal amplification (SPIA), and circular helicase-dependent amplification (cHDA).

In a number of applications, however, only a very low copy number of target nucleic acid sequences are present in the sample under investigation. The presence of only very low copy numbers of nucleic acid sequences in a sample provides a challenge to any existing nucleic acid amplification technique.

As an example, early detection of sepsis may become a key factor for the successful diagnosis and treatment of patient suffering from that disease. However, only very minute amounts of microbial cells in the blood of e.g. humans may be present even in life threatening conditions of sepsis. Thus, in particular the detection of target nucleic acid sequences originating from microbial organisms causing sepsis poses great challenges to molecular diagnostic tools.

Similarly, the detection of different markers in HIV-infected patients poses significant difficulties in detection and diagnosis.

In a number of diagnostic applications it is critical to provide a diagnostic result within the shortest possible time. For example, due to the very rapid progression of sepsis, a key factor in a successful diagnosis of sepsis is the speed at which a diagnosis may be finalised.

In the diagnosis of sepsis, the extremely low number of bacteria in the blood and the corresponding extremely low number of specific nucleic acid marker sequences often present a significant challenge to the nucleic acid detection technique used. Further, the need of simultaneous investigation of the presence of multiple target nucleic acid sequences, e.g. in the diagnosis of sepsis, provides a further challenge in that the samples must be subject to a technique capable of amplifying and detecting multiple mutually different target nucleic acid sequences. Often, there is a need for simultaneous amplification of 10 or more sequences.

Loop-mediated amplification has proven to be a rapid, sensitive and highly specific technique for amplification of nucleic acid target sequences. However, even loop-mediated nucleic acid amplification has proven to be incapable in a number of applications, i.e. with an unsatisfactory sensitivity. Further, loop-mediated amplification cannot be used for the simultaneous detection of more than one target nucleic acid in a particular sample.

Nested PCR is a well-known technique, which provides a method of detecting very small amounts of target nucleic acid molecules in samples. The technique was introduced in order to circumvent the lack of sufficient sensitivity of conventional PCR. Nested PCR consists of a first step of PCR amplification of the target nucleic acid in the sample using a pair of primers targeted at the amplification of a nucleic acid sequence comprising the target sequence and a sequence upstream and downstream of the target, followed by a second step of PCR amplification of the target sequence. Thereby, a highly sensitive and specific detection of the target nucleic acid is achieved. However, nested PCR has proven to be time-consuming and practically difficult to handle in a number of applications. For example, multiplex nested PCR has shown to be difficult e.g. due to the multiple primer pairs required.

Existing techniques of multiplex detection of nucleic acid sequences, e.g. multiplex PCR, have in practice been difficult to operate with more than 3 or 4 target sequences. Further, multiplex PCR suffers to an even greater extent from the above described problems for PCR in general. Further, multiplex detection often requires that every target sequence is present in significant and approximately equal amounts in order to avoid an uneven amplification of the different target sequences. Assay approaches that split the initial specimen for parallel PCR reactions are often not feasible due to limited quantity of target DNA. Multiplex PCR using multiple primer sets in the same reaction may decrease specimen consumption but is limited in detection sensitivity.

Hence, the detection of several target sequences in e.g. the diagnosis of sepsis using multiplex PCR has turned out to be problematic.

Further, PCR is desirably to be avoided in a method suitable for use in a point-of-care system. This is primarily due to the requirement of temperature cycling, which may be problematic in a multiplex setting. Most of all, temperature cycling is problematic in the detection part or the detection sequence of steps in the method because measurement artefacts may be introduced by the presence of bubbles and/or the entire sample may be difficult to focus.

Accordingly, a method suitable for use in a point-of-care test, which method can simultaneously detect multiple pathogens from a single specimen, and which method does not use PCR in the final amplification steps is highly desirable.

Accordingly, there is a need in the art for more sensitive molecular techniques for the detection of target nucleic acid sequences in a sample.

There is also a need in the art for less time-consuming molecular techniques for the detection of target nucleic acid sequences in a sample.

There is also a need in the art for molecular techniques capable of simultaneous detection of two or more mutually different target nucleic acid sequences in a sample.

In particular, there is a need in the art for molecular techniques that are more sensitive, less time-consuming and allow for the detection of two or more mutually different target nucleic acid sequences in a sample.

There is also a need in the art for new molecular techniques that are more easily subjected to automated operation, i.e. requiring a minimal amount of time and where final amplification and detection can be performed under isothermal conditions in the same operation and within the same reaction vessel.

In the art of the diagnosis of bacteria related to sepsis, the above mentioned needs are especially pronounced.

It is therefore an object of the present invention to provide a simple and highly sensitive method of detecting the presence or absence of a target nucleic acid sequences in a sample.

It is a further object of the invention to provide a rapid method of detecting the presence or absence of a target nucleic acid sequences in a sample.

It is a further object of the present invention to provide a method of detecting the presence or absence of two or more mutually different target nucleic acid sequences in a sample.

It is a further object of the present invention to provide a method of detecting the presence or absence of two or more mutually different target nucleic acid sequences in a sample, the method being capable of detecting the presence or absence of very small amounts of target molecules in the sample.

It is further an object to provide a method for the amplification of two or more target molecule sequences related to the diagnosis of sepsis.

It is further an object of the invention to provide an amplification technique that is more easily subjected to automated operation, i.e. requiring a minimal amount of time and where final amplification and detection may be performed under isothermal conditions in the same operation and within the same reaction vessel.

DISCLOSURE OF THE INVENTION

During the experiments leading to the present invention, it was surprisingly found that the above objects of the invention could be achieved by combining the techniques of PCR amplification and an amplification resembling a loop-mediated amplification into a single amplification method. The inventive method thus consists of a first sequence of steps comprising a PCR pre-amplification of the target nucleic acid sequence followed by a second sequence of steps comprising a reaction resembling a loop-mediated amplification and isothermal detection of the pre-amplified sample.

Thus, the present invention relates to a new amplification technique, which the inventors have termed "isoPCR". The technology in its simplest form is a two-step amplification technology where target sequences from the first PCR step are used to initiate a specific second nested isothermal amplification step, where each discrete target sequence is further amplified in a defined location.

The invention is highly useful in a point-of-care method and device since the final amplification and detection part of the method may be performed under isothermal conditions.

Accordingly, in a first aspect, the present invention relates to a method for detecting the presence or absence of one or more target nucleic acid sequences in a sample, the method comprising the steps of:
  a. providing a sample
  b. optionally extracting nucleic acid sequences from the sample, thereby providing a nucleic acid extract sample
  c. providing, for each one or more target nucleic acid sequences, a pair of nucleic acid primers, said pair of primers comprising a primer (a) having a 3' part (a1) that is substantially complementary to a part of the target sequence the presence or absence of which is to be detected, or a sequence downstream (3') thereof, and a primer (b) having a 3' part (b1) that is substantially homolog to a part of the target sequence, the presence or absence of which is to be detected, or a sequence upstream (5') thereof, the pair of nucleic acid primers (a) and (b) being suitable for use in a polymerase chain reaction (PCR) mediated amplification of a nucleic acid sequence comprising the target nucleic acid sequence
  d. providing, for each one or more target nucleic acid sequences, a pair of nucleic acid primers, said pair of primers comprising a primer (c) having a 3' part (c1) that is substantially complementary to a first part of the target sequence, the presence or absence of which is to be detected, and a 5' part (c2) that is substantially homolog to a second part of the target sequence, said second part of the target nucleic acid sequence being located upstream (5') of the first part of the target sequence, and a primer (d) comprising a 3' part (d1) that is substantially homolog to a fourth part of the target sequence the presence or absence of which is to be detected and a 5' part (d2) that is substantially complementary to a third part of the target sequence, said third part being located upstream (5') of the second part, and said fourth part being located upstream (5') of the third part of the target nucleic acid sequence, the set of nucleic acid primers (c) and (d) being suitable for use in a loop mediated amplification reaction for amplifying the target nucleic acid sequence e. optionally providing, for each one or more target nucleic acid sequences, nucleic acid primers e) and/or f), the primer e) having a 3' part (e1) that is substantially homolog to a fifth part of the target sequence, said fifth part being located upstream (5') of the first part, and downstream (3') of the second part of the target nucleic acid sequence, the primer f) having a 3' part (f1) that is substantially complementary to a sixth part of the target sequence said sixth part being located upstream (5') of the third part, and downstream (3') of the fourth part of the target nucleic acid sequence f. subjecting the sample of step a or b to at least one cycle of polymerase chain reaction (PCR) amplification in the presence of the one or more pairs of nucleic acid primers provided in step c, whereby a pre-amplified sample is provided, wherein the amount of the one or more target nucleic acid sequences in the samples is increased g. subjecting the pre-amplified sample of step f, or a subsample thereof, to a loop-mediated amplification reaction, using a pair of nucleic acid primers provided in step d and optionally one or more of the primers provided in step e, thereby providing a sample reaction product h. detecting the presence or absence of a nucleic acid amplification product in the sample reaction product of step g using conventional techniques.

In a particular embodiment, the method according to the invention is a method for detecting the presence or absence of two or more mutually different target nucleic acid sequences in a sample, the method comprising the above steps a-h, and further comprising an additional step of dividing the pre-amplified sample of step f into two or more subsamples and subjecting the two or more subsamples to the process of steps g and h.

This embodiment is highly useful in a point-of-care method and device, since the PCR part of the method may be performed as a multiplex reaction in a single compartment followed by final isothermal amplification in multiple compartments (one compartment per target sequence).

Definitions

PCR

The polymerase chain reaction (PCR) was developed in 1983 and is a technique to amplify a single or a few copies of a piece of DNA across several orders of magnitude, generating thousands to millions of copies of a particular DNA sequence. The method relies on thermal cycling, consisting of cycles of repeated heating and cooling of the reaction for DNA melting and enzymatic replication of the DNA. Primers consisting of short DNA fragments containing sequences complementary to the target region anneal to a single stranded target sequence and allow a DNA polymerase to initiate DNA synthesis. As PCR progresses, the DNA generated is itself used as a template for replication, setting in motion a chain reaction in which the DNA template is exponentially amplified. The technique is well-known to the skilled person.

LAMP

Loop-mediated amplification (LAMP) is a DNA amplification technique developed by Notomi T, et al., (Notomi et al., 2000. Loop-mediated isothermal amplification of DNA. Nucleic Acids Research 28:E63). Using LAMP, the target nucleic acid sequence is amplified at a constant temperature of 60-65° C. using either two or three pairs of primers and a polymerase with high-strand displacement activity in addition to a replication activity. The loop-mediated isothermal amplification (LAMP) reaction is a highly specific, sensitive, isothermal nucleic acid amplification reaction. LAMP employs a primer set of four essential primers, termed forward inner primer (FIP), backward inner primer (BIP), forward displacement primer (F3) and backward displacement primer (B3). These four different primers are used to identify 6 distinct regions on the target gene, which adds highly to the specificity. Due to the specific nature of the action of these primers, the amount of DNA produced in LAMP is considerably higher than PCR-based amplification. Furthermore, two optional primers can be included which effectively accelerate the reaction; these are termed forward loop primer (LF) and backward loop primer (LB). The inner primers (FIP and BIP) contain sequences of the sense and antisense strands of the target DNA, while the displacement primers (F3 and B3) and the loop primers (LF and LB) each contain a single target sequence. In tota, eight target sequences are recognized when including loop primers (LF and LB) in the reaction. A DNA polymerase is used to amplify the target sequence of interest. Many different DNA polymerases may be used, the most common being the Bst DNA polymerase while the *Geobacillus* sp. large fragment (GspSSD) DNA polymerase is used less often.

The LAMP reaction is initiated by DNA synthesis primed by the inner primers (FIP and BIP). This is followed by DNA synthesis primed by a displacement primer (F3 or B3) which releases a single-stranded DNA. This single-stranded DNA serves as template for DNA synthesis primed by the second inner and displacement primers that hybridize to the other end of the target. This produces a stem-loop DNA structure. In subsequent LAMP cycling, one inner primer hybridizes to the loop on the product and initiates displacement DNA synthesis. This yields the original stem-loop DNA and a new stem-loop DNA with a stem twice as long. The cycling reaction continues with accumulation of around $10^9$ copies of target in less than an hour. The inclusion of one or two loop primers (LF and/or LB) accelerates the LAMP reaction by hybridizing to the stem-loops, except for the loops that are hybridized by the inner primers, and prime strand displacement DNA synthesis. A variety of LAMP amplification detection methods exist. Non-specific target detection may be obtained through visual identification of a turbid sample as magnesium pyrophosphate precipitates in a positive LAMP reaction. For better visibility of a positive reaction, various agents, such as hydroxy naphthol blue or calcein, may be added to the reaction. Alternatively, fluorescent detection may be achieved using a DNA intercalating dye, such as SYBR green, Picogreen or propedium iodide, which is added to the reaction reagent or added after the completion of the reaction for end point analysis.

Detecting the amplification of a specific target of interest by the LAMP reaction may be achieved using various hybridization probe-based methods. For example, by labelling a loop primer with a fluorophore and adding a DNA probe which is complementary to the loop primer but labelled with a quencher molecule. Initially, the loop primer will bind the DNA probe, and the fluorophore will not emit light. When the LAMP reaction proceeds, the loop primer is incorporated into the stem-loop structure and the DNA probe cannot quench the fluorophore resulting in a fluorescent signal. LAMP products may also readily be identified using gel electrophoresis which visualizes distinct banding patterns depending on the specific target and primers used. The technique is well-known to the skilled person and described in detail e.g. in Nagamine et al., Molecular and Cellular Probes (2002) 16, 223-229.

LAMP-Type Amplification Reaction

According to the present invention, the step of isothermal amplification of the PCR pre-amplified sample (step g), is termed a LAMP-type isothermal amplification reaction. In all aspects, this reaction resembles a typical LAMP reaction, except that only one pair of primers is required. These required primers correspond to the inner primers FIP and BIP as described above. The displacement primers (F3 and B3) that are essential in a conventional LAMP reaction do not have any function in the isothermal amplification according to the present invention. While the LAMP-type amplification according to the seventh step of the present invention contains some elements of LAMP, it represents a simplification and acceleration when compared to classical LAMP.

According to the present invention, "sequence" means an oligonucleotide chain of DNA or RNA of at least 5 nucleic acids. However, alternative nucleotide analogs such as LNA or other similar analogs may be incorporated in the target sequence and/or in the primer sequences.

According to the present invention, "complementary" or the phrase "complementary sequence" is used to describe the relationship between two nucleic acid sequences where one sequence will anneal to the other sequence under suitable conditions (below the melting point of the sequence) in such a way that the two sequences together form a conventional double stranded DNA molecule wherein the two strands are orientated in different 5'-3' directions. As an example, the sequence 5'AAGGTTCC3' is complementary to the sequence 5'GGAACCTT3'.

According to the present invention, the "homolog" or the phrase "homolog sequence" is used to describe the relationship between two nucleic acid sequences where one sequence has a sequence that is identical to the other sequence when the two sequences are orientated in the same 5'-3' directions. As an example, the sequence 5'AAGGTTCC3' is homolog to the sequence 5'AAGGTTCC3'.

According to the present invention, "substantially" used in connection with "homolog" or the phrase "homolog sequence" or the word "complementary" or the phrase "complementary sequence" is used to describe a situation where at least 80% of the nucleotides in the sequence are complementary/homolog, respectively. In a preferred definition, "substantially" used in connection with "homolog" or the phrase "homolog sequence" or the word "complementary" or the phrase "complementary sequence" is used to describe a situation where at least 80% of the nucleotides in the sequence are complementary/homolog respectively. In another preferred definition, sequences comprising less than 3 non-complementary/non-homolog nucleotides are "substantially" complementary/homolog. In a more preferred definition, sequences comprising less than 2 non-complementary/non-homolog nucleotides are "substantially" complementary/homolog.

According to the present application, "primer" means an oligonucleotide comprising at least 5 nucleic acids being complementary to a specific region of nucleic acids in or adjacent to the target sequence. Primers must be capable of initiating DNA synthesis by a DNA polymerase.

The phrase "a pair of nucleic acid primers" means at least two oligonucleotides being suitable for use in a polymerase mediated amplification of the relevant target nucleic acid sequence. The pair of primers are suitable for use in a polymerase mediated amplification of the relevant target nucleic acid sequence if one of the primers comprises a 3' part that is substantially complementary to a part of the target nucleic acid sequence and the other primer comprises a 3' part that is substantially identical to a part of the target nucleic acid sequence.

DETAILED DESCRIPTION OF THE INVENTION

Figure 1:
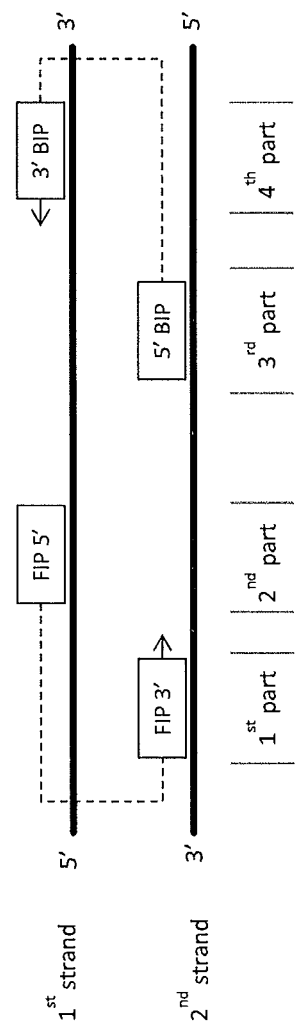
FIG. 1 shows the primer design of the L-primers according to the invention. Arrows show direction of primer extension DNA synthesis. The first L-primer (c) comprises the two parts FIP 3' (part c1) and FIP 5' (part c2). The second L-primer (d) comprises the two parts BIP 3' (part d1) and BIP 5' (part d2). The dotted lines indicate that the parts are connected in a single primer sequence. The FIP 3' part (c1) is complementary to the first part of the target sequence (present on the second) and the FIP 5' part (c2) is homolog to the second part of the target sequence (present on the second strand). Further, the BIP 3' part (d1) is homolog to the fourth part of the target sequence (present on the second strand) and the BIP 5' part (d2) is complementary to the third part of the target sequence (present on the second strand).

It was surprisingly observed that combining the amplification technique of PCR and a loop mediated type isothermal amplification in a single assay was capable of fulfilling the objects of the invention. The new PCR/isothermal amplification-based technology was named "isoPCR" and combined the advances from PCR and isothermal amplification.

In its broadest sense, the isoPCR technology is a two-step amplification technology where target sequences from a first PCR step are used to initiate the second nested isothermal amplification step. In a first step, multiplex target sequences are generated each using one specific primer set, with all reactions taking place in one tube. In a second step, the reaction product of the first step, or a small portion of the first reaction product, is transported to several single amplification zones, where each discrete target sequence is further amplified in an isothermal amplification step driven by a second primer pair in a defined location.

Due to the use of at least one primer pair being targeted at (collectively) 4 regions in the target nucleic acid (the primer pair used in the isothermal amplification step must target 4 regions), the isoPCR has specificity which is comparable to nested PCR. Specificity may be increased by using different primer pairs in the PCR and the isothermal step according to the invention. Ease of procedure may be obtained by using similar primer pairs in the PCR and the isothermal step according to the invention.

Accordingly, in a first aspect, the present invention relates to a method for detecting the presence or absence of one or more target nucleic acid sequences in a sample, the method comprising the steps of:

a. providing a sample
b. optionally extracting nucleic acid sequences from the sample, thereby providing a nucleic acid extract sample
c. providing, for each one or more target nucleic acid sequences, a pair of nucleic acid primers, said pair of primers comprising a primer (a) having a 3' part (a1) that is substantially complementary to a part of the target sequence, the presence or absence of which is to be detected, or a sequence downstream (3') thereof, and a primer (b) having a 3' part (b1) that is substantially homolog to a part of the target sequence, the presence or absence of which is to be detected, or a sequence upstream (5') thereof, the pair of nucleic acid primers (a) and (b) being suitable for use in a polymerase chain reaction (PCR) mediated amplification of a nucleic acid sequence comprising the target nucleic acid sequence
d. providing, for each one or more target nucleic acid sequence, a pair of nucleic acid primers, said pair of primers comprising a primer (c) having a 3' part (c1) that is substantially complementary to a first part of the target sequence, the presence or absence of which is to be detected, and a 5' part (c2) that is substantially homolog to a second part of the target sequence, said second part of the target nucleic acid sequence being located upstream (5') of the first part of the target sequence, and a primer (d) comprising a 3' part (d1) that is substantially homolog to a fourth part of the target sequence the presence or absence of which is to be detected and a 5' part (d2) that is substantially complementary to a third part of the target sequence, said third part being located upstream (5') of the second part, and said fourth part being located upstream (5') of the third part of the target nucleic acid sequence, the set of nucleic acid primers (c) and (d) being suitable for use in a loop-mediated amplification reaction for amplifying the target nucleic acid sequence
e. optionally providing, for each one or more target nucleic acid sequence, nucleic acid primers e) and/or f), the primer e) having a 3' part (e1) that is substantially homolog to a fifth part of the target sequence, said fifth part being located upstream (5') of the first part, and downstream (3') of the second part of the target nucleic acid sequence, the primer f) having a 3' part (f1) that is substantially complementary to a sixth part of the target sequence, said sixth part being located upstream (5') of the third part, and downstream (3') of the fourth part of the target nucleic acid sequence
f. subjecting the sample of step a or b to at least one cycle of polymerase chain reaction (PCR) amplification in the presence of the one or more pairs of nucleic acid primers provided in step c, whereby a pre-amplified sample is provided, wherein the amount of the one or more target nucleic acid sequences in the samples is increased
g. subjecting the pre-amplified sample of step f, or a subsample thereof, to a loop-mediated amplification reaction, using a pair of nucleic acid primers provided in step d, and optionally, one or more of the primers provided in step e, thereby providing a sample reaction product
h. detecting the presence or absence of a nucleic acid amplification product in the sample reaction product of step g using conventional techniques.

Step a

In the first step (step a) of the method, a sample is provided. Preferably the sample is of human origin. In one embodiment of the invention, the sample is a blood sample. In another embodiment of the invention, the sample is a urine sample. In another embodiment of the invention, the sample is a swab sample from a human.

Step b

In the optional second step (step b), nucleic acids are isolated from the sample whereby amplification of nucleic acid sequences according to the invention may be more easily performed. Nucleic acids may be extracted from samples using conventional techniques. Such are well known to the skilled person and kits of parts suitable for nucleic acid extraction from samples are commercially available. However, often such procedures are time-consuming and in respect of particular embodiments, alternative simpler and faster procedures which only remove bulk of inhibiting substances will be preferred. In some embodiments, no nucleic acid extraction step is necessary and therefore not preferred.

Step c

In the third step of the method (step c), one or more pairs of primers (P-primers), each pair amplifying one or more target nucleic acid sequences, is provided. Each pair of primers must be suitable for use in a polymerase chain reaction (PCR) amplification of the relevant target sequence. The skilled person is familiar with the conventional design of such primer pairs. Each pair of primers must contain a forward primer (a) having a 3' part (a1) that is substantially complementary to a part of the target sequence, the presence or absence of which is to be detected, or a sequence downstream (3') thereof. Further, each pair of primers must contain a reverse primer (b) having a 3' part (b1) that is substantially homolog to a part of the target sequence, the presence or absence of which is to be detected, or a sequence upstream (5') thereof. Further, the pair of nucleic acid primers must be suitable for use in a polymerase chain reaction (PCR) mediated amplification of a nucleic acid sequence comprising the target nucleic acid sequence. The target sequence, including the first, second, third and fourth part thereof must therefore be amplified by the P-primers. Thus, the forward primer (a) must comprise a 3' part being complementary to a part of the first part of the target sequence or a sequence downstream (3') thereof. Likewise, the reverse primer (b) must comprise a 3' part being homolog to a part of the fourth part of the target sequence or a sequence upstream (5') thereof. Further, the 3' parts (a1) and (b1) of the pair of primers should be designed to target and amplify a sequence of a suitable length. A suitable length of PCR amplification product is preferably between 50 and 2000 bp.

The P-primers of each of the primer pairs should have a similar Tm (melting point), preferably deviating less than 10 degrees between P-primers within the pair. In a multiplex setting, the mutually different P-primer pairs should likewise have a similar Tm (melting point), preferably deviating less than 10 degrees between primers within mutually different pairs. Preferably, the P-primers provided in step c or the 3' parts (a1) and (b1) thereof have a Tm of between 40-80 degrees. The length of each of the (a1) and (b1) parts of the P-primers should be between 12 and 35 base pairs, preferable between 15 and 30 base pairs, even more preferably between 15 and 25 base pairs.

The pairs of P-primers provided are preferably mutually different, such that they target the pre-amplification of mutually different nucleic acid sequences in the sample.

However, in certain embodiments, it is only necessary or recommended to pre-amplify one of the target nucleic acid sequences in a sample, e.g. in situations where only one of the target sequences (if present) is present in a very low copy number. This may be relevant, e.g. in situations where one target sequence is a sequence present in a high copy number plasmid present in an organism which is to be detected, whereas another target sequence is a sequence only present in one copy in the organism which is to be detected.

Accordingly, in one embodiment of the invention the pairs of P-primers used in the pre-amplification target all of the nucleic acids sequences that are targeted in the subsequent isothermal amplification step. In one embodiment, only one of the target sequences in the sample is pre-amplified in the pre-amplification step.

In a further embodiment, one or more of the pairs of P-primers used in the pre-amplification step is capable of amplifying several mutually different target sequences. An example of such an embodiment is the pre-amplification of conserved regions, e.g. conserved regions of genes encoding ribosomal RNA, whereby a single primer pair is sufficient for the amplification of several mutually different target sequences. In such embodiment several of the target sequences in the sample are pre-amplified in the pre-amplification step, by use of one set of pre-amplification primers.

Step d

In the fourth step (step d) of the method, a pair of nucleic acid primers (L-primers) for each one or more target nucleic acid sequences is provided. Preferably each pair of primers is specifically designed to amplify only one of the pre-amplified target sequences produced in the third step of the method. The general design of the pair of L-primers is shown in FIG. 1, wherein the second strand comprises the target sequence present in a double stranded molecule. The pair of L-primers comprise a primer (c) having a 3' part (c1) that is substantially complementary to a first part of the target sequence, the presence or absence of which is to be detected, and a 5' part (c2) that is substantially homolog to a second part of the target sequence, said second part of the target nucleic acid sequence being located upstream (5') of the first part of the target sequence. The pair of L-primers further comprise a primer (d) comprising a 3' part (d1) that is substantially homolog to a fourth part of the target sequence, the presence or absence of which is to be detected, and a 5' part (d2) that is substantially complementary to a third part of the target sequence, said third part being located upstream (5') of the second part, and said fourth part being located upstream (5') of the third part of the target nucleic acid sequence. The pair of nucleic acid L-primers (c) and (d) must be suitable for use in a loop mediated amplification reaction for amplifying the target nucleic acid sequence. This means that the primers must be able to form a reaction product in a loop-mediated isothermal reaction under appropriate isothermal conditions.

The parts of the L-primers (c1), (d1), (c2) and (d2) of each of the primer pairs preferably have a similar Tm (melting point), preferably deviating less than 10 degrees between parts of the primers within each pair.

Preferably, the parts of the primers (c1), (d1), (c2) and (d2) provided in step d each have a Tm of between 45-75 degrees, even more preferably between 58 and 68 degrees.

The length of each of the (c1), (d1), (c2) and (d2) parts of the L-primers is preferably between 12 and 35 base pairs, preferable between 15 and 30 base pairs, even more preferably between 18 and 22 base pairs.

The pairs of L-primers provided are preferably mutually different, such that they target the isothermal amplification of mutually different nucleic acid sequences in the sample.

In one embodiment the L-primers and the P-primers are identical (see example 1).

Step e

In the optional fifth step (step e) of the method one or more primers e) and/or f), preferably a pair of primers e) and f) are provided, for each one or more target nucleic acid sequence. In the following, these are termed O-primers. The nucleic acid O-primer e) has a 3' part (e1) that is substantially homolog to a fifth part of the target sequence, said fifth part being located upstream (5') of the first part and downstream (3') of the second part of the target nucleic acid sequence. The 0-primer f) has a 3' part (f1) that is substantially complementary to a sixth part of the target sequence said sixth part being located upstream (5') of the third part, and downstream (3') of the fourth part of the target nucleic acid sequence.

The O-primers preferably have a Tm (melting point) similar to the corresponding parts of the L-primers (c1), (d1), (c2) and (d2) of each of the primer pairs, preferably deviating less than 10 degrees between parts of the primers within each pair.

Preferably, the O-primers (e) and (f) (d1), optionally provided in step e have a Tm of between 45-75 degrees, even more preferably between 58 and 68 degrees.

The length of each of O-primers is preferably between 12 and 35 base pairs, preferable between 15 and 30 base pairs, even more preferably between 18 and 22 base pairs.

Step f

In the sixth step (step f) of the method (the PCR pre-amplification step) the sample of step a or the nucleic acid extract therefrom provided in step b is subjected to at least one cycle of polymerase chain reaction (PCR) amplification in the presence of at least one of the pairs of nucleic acid primers provided in step c. Thereby, a pre-amplified sample is provided, wherein the amount of at least one of the two or more target nucleic acid sequences in the samples is increased. The PCR is suitably performed in a conventional way using conventional techniques and reaction ingredients. In a preferred embodiment, the pre-amplified sample is divided into two or more samples before proceeding with the seventh step of the method with the subsample as template.

Preferably, the pre-amplification proceeds in at least 5 PCR cycles, more preferably at least 9 PCR cycles. Preferably, the pre-amplification proceeds in less than 25 PCR cycles, more preferably less than 20 PCR cycles. Preferably, the pre-amplification step of the method comprises between 10 and 19 PCR temperature cycles, even more preferably between 10 and 15 PCR cycles.

Step g

In the seventh step (step g) of the method, the pre-amplified sample of step f, or a subsample thereof, is subjected to an isothermal loop-mediated type amplification reaction, using a pair of nucleic acid primers provided in step d and optionally, one or more of the primers provided in step e, thereby providing a sample reaction product. The simultaneous use of the primers provided in step e results in a faster amplification, and in an increased sensitivity. However, it has surprisingly been shown that the O-primers provided in step e are not essential to the performance of the assay. Omitting the O-primers thus provides the benefit of a simpler amplification system and a simpler assay design. The DNA polymerase used in this step must be a polymerase capable of strand displacement. A suitable polymerase could be the Bst DNA polymerase or the *Geobacillus* sp. Large Fragment DNA polymerase. Further the conditions in the sixth step resemble the conditions used in conventional loop mediated isothermal amplification procedures. These conditions are well-known to the skilled person.

Step h

In the eight step of the method (step h), the presence or absence of a nucleic acid amplification product in each one or more sample reaction products produced in step g is detected. This may be performed using conventional techniques.

Preferably, the seventh and eight step are performed as a single step wherein the amplification product is monitored (step h) as the amplification reaction according to the seventh step (step g) proceeds. This may for example be performed by monitoring the release of pyrophosphate corresponding to the progression of the amplification reaction. The release of pyrophosphate results in visible turbidity due to precipitation, which allows easy visualization by the naked eye, especially for larger reaction volumes or via simple detection approaches for smaller volumes. Thus, preferably, the reaction is followed in real-time either by measuring the turbidity or by monitoring the signals arising from the presence of (added) fluorescent dyes that intercalate or directly label the DNA, and in turn may be correlated to the number of copies initially present.

Further, if a thermostable polymerase having displacement activity could be provided, such polymerase would provide the possibility of performing steps f and g (or f, g and h) in a single one type reaction. Such embodiment would be highly desirable.

It was also surprisingly observed that the method according to the invention provided a more consistent result (with a smaller variance between results) from identical samples than results based on PCR or Nested PCR. This unexpected result may, without being bound by theory, be a result of the removal of gas and air bubbles resulting from the combination of PCR and isothermal amplification according to the invention.

Further Embodiments

In contrast to conventional loop-mediated amplification techniques, it was surprisingly observed that the amplification technique according to the invention was suitable for providing isothermal amplification of multiple targets present in very low copy numbers in samples. The detection of two or more targets could be easily accomplished when performing a pre-amplification using PCR followed by dividing the amplification product into subsamples which are subsequently used in the next amplification and detection steps. Thus, in a particular embodiment, the inventive method is a method for detecting the presence or absence of two or more mutually different target nucleic acid sequences in a sample, the method comprising the above steps a-h, and further comprising the additional step of dividing the pre-amplified sample of step f into two or more subsamples and subjecting the two or more subsamples to the process of steps 7 and 8.

Further, it was surprisingly found that this method was capable of providing a result much faster than a corresponding Nested PCR approach.

Further, it was observed that the amplification process according to the invention was superior in the detecting target nucleic acid sequences related to sepsis.

Accordingly, in a particular embodiment, the invention relates to a method for detecting the presence or absence of two or more mutually different target nucleic acid sequences in a sample, the method comprising the steps of:

a. providing a sample
b. optionally extracting nucleic acid sequences from the sample, thereby providing a nucleic acid extract sample
c. providing, for each two or more target nucleic acid sequences, a pair of nucleic acid primers, said pair of primers comprising a primer (a) having a 3' part (a1) that is substantially complementary to a part of the target sequence, the presence or absence of which is to be detected, or a sequence downstream (3') thereof, and a primer (b) having a 3' part (b1) that is substantially homolog to a part of the target sequence, the presence or absence of which is to be detected, or a sequence upstream (5') thereof, the pair of nucleic acid primers being suitable for use in a polymerase chain reaction (PCR) mediated amplification of a nucleic acid sequence comprising the target nucleic acid sequence
d. providing, for each two or more target nucleic acid sequence, a pair of nucleic acid primers, said pair of primers comprising a primer (c) having a 3' part (c1) that is substantially complementary to a first part of the target sequence, the presence or absence of which is to be detected, and a 5' part (c2) that is substantially homolog to a second part of the target sequence, said second part of the target nucleic acid sequence being located upstream (5') of the first part of the target sequence, and a primer (d) comprising a 3' part (d1) that is substantially homolog to a fourth part of the target sequence, the presence or absence of which is to be detected, and a 5' part (d2) that is substantially complementary to a third part of the target sequence, said third part being located upstream (5') of the second part, and said fourth part being located upstream (5') of the third part of the target nucleic acid sequence, the set of nucleic acid primers (c) and (d) being suitable for use in a loop-mediated amplification reaction for amplifying the target nucleic acid sequence
e. optionally providing, for each two or more target nucleic acid sequences, nucleic acid primers e) and/or f), the primer e) having a 3' part (e1) that is substantially homolog to a fifth part of the target sequence, said fifth part being located upstream (5') of the first part, and downstream (3') of the second part of the target nucleic acid sequence, the primer f) having a 3' part (f1) that is substantially complementary to a sixth part of the target sequence, said sixth part being located upstream (5') of the third part, and downstream (3') of the fourth part of the target nucleic acid sequence
f. subjecting the sample of step a or b to at least one cycle of polymerase chain reaction (PCR) amplification in the presence of the two or more pairs of nucleic acid primers provided in step c, whereby a pre-amplified sample is provided, wherein the amount of the one or more target nucleic acid sequences in the samples is increased, which pre-amplified sample is divided into two or more subsamples
g. subjecting each of the two or more pre-amplified subsamples of step f to a loop-mediated amplification reaction, each of the reactions using one of the target specific pairs of nucleic acid primers provided in step d, and optionally, one or more of the corresponding target specific primers provided in step e, thereby providing two or more target specific sample reaction products
h. detecting the presence or absence of a nucleic acid amplification product in each of the sample reaction products of step g using conventional techniques.

It was surprisingly observed that the method according to the invention could be used for detecting the presence or absence of multiple targets. Unlike for example conventional multiplex PCR, which in practice is limited by a number of factors to the simultaneous detection of 4-5 different targets when using the number of amplification cycles required for generating a detectable amount of amplification product, the present invention was surprisingly not limited in this respect. It was speculated that this was due to the limited amount of PCR cycles required in the pre-amplification step according to the present invention.

Thus, in a preferred embodiment of the invention, the invention relates to a method for detection of three or more nucleic acid target sequences, such as four or more, such as five or more, such as six or more, such as seven or more nucleic acid target sequences. Thus, the invention relates to a method of detecting 3-40, such as 4-40, such as 5-40, such as 6-40, or such as 4-25, such as 5-20, such as 5-15 mutually different target sequences. In these embodiments, for each mutually different target sequence, a pair of P-primers according to the third step of the method suitable for PCR amplification of the target sequence is provided, and for each mutually different target sequence, a pair of L-primers according to the fourth step of the method and suitable for loop-mediated amplification of the target sequence is provided. Further, optionally, O-primers for each mutually different target sequence may be provided. These primer pairs are then used in the reaction steps f-h of the method.

In this embodiment of the invention, the P-primer pairs provided according to the third step of the method need not be specific to a single target nucleic acid sequence. For example, a single pre-amplification P-primer pair may amplify multiple mutually different target sequences. For example, the primers provided in the third step may be targeted at generic or conserved regions amplifying multiple different targets, such as ribosomal target sequences, or other conserved regions of interest.

The L-primer pairs provided according to the fourth step of the method, however, are preferably specific to a single of the target nucleic acid sequences pre-amplified in step f.

In a preferred embodiment of the invention, the first and the second part of the target sequence are separated by at least 12 nucleic acid bases. Further, in a preferred embodiment, the third and the fourth part of the target sequence are separated by at least 12 nucleic acid bases. Thereby, a loop is formed in the single-stranded amplification products produced during the seventh step of the inventive method, whereby the reaction proceeds at a faster rate. This is especially preferred when using the optional O-primers provided in step e. These primers then target a region (the fifth part) between the first and second part and/or a region (sixth part) between the third and fourth part of the target sequence.

In a preferred embodiment, the fifth part of the target nucleic acid sequence does not comprise parts of the first and the second part of the target sequence, and wherein the sixth part of the target nucleic acid sequence does not comprise parts of the third and the fourth part of the target nucleic acid sequence. Thereby, the action of the optional O-primers is less hindered by double-stranded DNA.

In another preferred embodiment, the fifth part of the target nucleic acid sequence comprises parts of the first and parts of the second part of the target sequence. In a further preferred embodiment, the sixth part of the target nucleic acid sequence comprises parts of the third and parts of the fourth part of the target nucleic acid sequence.

In another preferred embodiment, the fifth part of the target nucleic acid sequence consists of parts of the first and parts of the second part of the target sequence. In a further preferred embodiment, the sixth part of the target nucleic acid sequence consists of parts of the third and parts of the fourth part of the target nucleic acid sequence.

It was surprisingly shown that the isoPCR reaction according to the present invention could be performed when the P-primers used in the PCR pre-amplification step comprised (as the 3' part), or consisted of, the same sequence as the 3' part of the L-primers. Thereby, a much more simple primer design can be envisaged, and the number of potential target sequences possible to amplify is increased. As an example, detection of shorter DNA sequences may be achieved. The minimum LAMP detection sequence is shortened by, at least, the length of the F3 and B3 primers that are essential to conventional LAMP, i.e. around 40 nucleotides.

Accordingly, in a preferred embodiment of the invention, the nucleic acid primer a) provided in step c comprises a 3' part that is substantially identical to the 3' part (c1) of the nucleic acid primer c) provided in step d. Similarly, in a preferred embodiment of the invention the nucleic acid primer b) provided in step c comprises a 3' part that is substantially identical to the 3' part (d1) of the nucleic acid primer d) provided in step d. The primers (a) and (b) may, for specific purposes, contain other 5' sequences, without deviating from this embodiment.

However, in an even more preferred embodiment of the invention, the nucleic acid primer (a) provided in step c is substantially identical to the 3' part (c1) of the nucleic acid primer c) provided in step d. Similarly, in a preferred embodiment of the invention the nucleic acid primer b) provided in step c is substantially identical to the 3' part (d1) of the nucleic acid primer d) provided in step d.

In an even more preferred embodiment of the invention, the nucleic acid primer a) provided in step c is substantially identical to the nucleic acid primer c) provided in step d. Similarly, in a preferred embodiment of the invention, the nucleic acid primer b) provided in step c is substantially identical to the nucleic acid primer d) provided in step d.

In an even more preferred embodiment of the invention, the nucleic acid primer a) provided in step c is identical to the nucleic acid primer c) provided in step d. Similarly, in a preferred embodiment of the invention the nucleic acid primer b) provided in step c is identical to the nucleic acid primer d) provided in step d. As seen in the examples (example X), this embodiment was surprisingly capable of providing an amplification product in the isoPCR method and thereby paves the way for easier assay design wherein only one pair of primer for each target sequence is necessary in order to provide an amplification product. Thereby, the isoPCR amplification reaction according to the invention may proceed using only one primer pair per target sequence. Accordingly, in one highly preferred embodiment of the invention, the only primers used in the assay are the L-primers, which are used also in the pre-amplification PCR step.

As seen in the examples the use of the additional primers (O-primers) e) and f) provides a faster isothermal reaction. Accordingly, in a preferred embodiment of the invention, the optional step e is performed and the provided O-primers are used in the reaction in step g.

In a preferred embodiment, one or both of the L-primer c) and d) provided in step d comprises a central linker sequence between the 3' and the 5' part, preferably consisting of at least 4 nucleotides, wherein the central linker sequence is not complementary or homolog to the target sequence.

Diagnostic Assay

From the clinical perspective, a point of care (FOC) test which can simultaneously detect multiple pathogens from a single specimen would be highly desirable. Test design strategies include comprehensive identification of all clinically-relevant pathogens which may be readily adapted to local epidemiology and other clinical factors.

Assay approaches that split the initial specimen for parallel simplex PCRs, each with a single primer set specific for a pathogen, are often not feasible due to limited quantity of target DNA. In addition to challenges in sensitivity, the fluidics of PCR in microfluidic systems are still in the early stage development. Alternatively, multiplex PCR using multiple primer sets in the same reaction can decrease specimen and reagent consumption but is limited in detection sensitivity due to inherent variability of amplification efficiencies of the different primer sets.

As an example, the diagnosis of sepsis is both complicated (involving several possible target sequences) and problematic due to the very low abundance of nucleic acid in samples of blood in humans. Accordingly, the present invention is highly suited for this assay. In a highly preferred embodiment of the invention, the one or more target nucleic acid sequences originate from a microorganism involved in sepsis.

In a preferred embodiment, the target sequence originates from one or more microorganisms selected among *Pseudomonas aeruginosa, Staphylococcus aureus, Candida albicans* and *Candida glabrata*.

The isoPCR method may also be used with superior results in other conventional assays such as the e.g. the assay for detection of the plasmid DNA for *Chlamydia trachomatis* (CT) and the genomic DNA of *Neisseria gonorrhoeae* (NG) in swab or urine specimens. This assay target two regions on the CT plasmid in order to detect the wild type CT strain (wtCT) and a Swedish, new variant CT strain (nvCT). Further, a single conserved region is targeted in the opa gene of NG. Finally, an internal control is added to the sample preparation, thereby a total of four regions are targeted in each assay run.

The target sequence or sequences may also be cDNA. Such target sequences may be provided by reverse transcribing RNA. Using the isoPCR method according to the present invention for detecting the expression level of one or more particular human RNA molecules in human peripheral blood, a reverse transcription step is required to translate the RNA molecule to a single stranded cDNA molecule, before the isoPCR method can be applied. Methods of reverse transcribing RNA are well known to the skilled person. Thereby the isoPCR method may be used with superior results in conventional human assays such as gene expression assays (testing particular genes at transcriptional level) in e.g. human peripheral blood. Gene expression assay measures the activity of specific mRNA molecules known to be involved in the development and progression of a particular disease, and thereby provides information about a person's current state of disease. Examples of such diseases are atherosclerosis and cardiovascular diseases.

Such diagnostic assays may preferably be provided as kits of parts intended for point of care use.

Accordingly, the present invention also relates to a kit of parts comprising one or more sets of nucleic acid primers a), b), and c) and d) as defined in the above embodiments.

A preferred embodiment of these kits comprises two or more sets of primers a), b), and c) and d).

EXAMPLES

Example 1

The objective of Example 1 was to investigate if PCR-pre-amplification of a target sequence from the organism *Candida glabrata* may be performed using some of the primers conventionally used for LAMP amplification of the same target sequence. Further, the objective was to investigate if such PCR pre-amplified sample could be further amplified using LAMP-like procedures and using the same primers.

A sample comprising purified DNA from 100 copies of *Candida glabrata* (produced using conventional techniques) was assayed together with a control sample without template target sequence (NTC=no template control (H2O)).

A pair of primers conventionally used for LAMP amplification of the target *Candida glabrata* sequence were designed and produced. The FIP primer had the sequence (5'-3') CTGCATTCCCAAACAACTCGACTCATG-GAGGGTGAGAATCCCG (SEQ ID NO: 1), and the BIP primer had the sequence TACAGGCGAGAGACCGA-TAGCGTTTCACTCTCTTTTCAAAGTTC (SEQ ID NO: 2). These primers correspond to the primers (c) and (d) in the method according to the invention. The primers FIP and BIP were then used both in the PCR step an in the LAMP-like step according to the invention.

A PCR reaction using FIP and BIP as primers was performed as follows. PCR reagent mixture (20 µL) consisted of: 2 µL purified DNA from *Candida glabrata* or $H_2O$ for no template control; 10 µl of 2× Mastermix TrueHOT (VWR); 0.4 µM of FIP and BIP primers, respectively. Using a thermocycler, the PCR reagent mixture was subjected to an initial hot-start of 15 minutes at 95° C., followed by 12 thermocycles of 30 seconds at 95, 30 seconds at 60° C. and 45 seconds at 72° C., final elongation was performed for 5 minutes at 72° C.

No PCR product could be observed on ethidium bromide stained agarose gels following electrophorese of the product.

The PCR reaction product was subsequently amplified using an isothermal loop-mediated amplification type of reaction using only primers FIP and BIP. Detection was performed using real-time fluorescent measurements. The amplification reaction mixture (25 µL) consisted of: 15 µL of Isothermal Mastermix (Optigene); 2 µL of first-stage PCR amplified product and 1.6 µM of FIP and BIP, respectively. Reactions were performed at 63° C. for 60 minutes using the Genie II device (Optigene). The device measured the development in fluorescent signal in real-time. The time for detection was determined by the associated software.

As a control, an isothermal reaction (no pre-amplification) was performed on purified DNA as template, which was identical to the template used in the two step PCR/LAMP detections described above.

Results

Surprisingly, a reaction product rapidly occurred in the PCR/LAMP assay, whereas no reaction product could be observed in the control sample. These results demonstrated that a pre-amplification product from a PCR using FIP and BIP primers may be used as templates in LAMP-like reactions in which the F3 and B3 (displacement primers) conventionally and essentially used in normal LAMP are left out.

Example 2

The objective of Example 2 was to compare the limit of detection (LOD) and time of detection for the conventional techniques qPCR, Nested PCR and LAMP with different embodiments of the combined PCR/LAMP assays according to the invention.

DNA purified from a dilution series of *Candida glabrata*, containing from 10,000 to 10 cells (copy numbers) per template sample, were produced using conventional techniques. These template samples were assayed together with a control sample without template target sequence (NTC=no template control (H2O)).

The primers targeting the template sequence from *Candida glabrata* were the following (5' to 3'):

```
FIP:
                                         (SEQ ID NO: 1)
CTGCATTCCCAAACAACTCGACTCATGGAGGGTGAGAATCCCG

BIP:
                                         (SEQ ID NO: 2)
TACAGGCGAGAGACCGATAGCGTTTCACTCTCTTTTCAAAGTTC

FIP3':
                                         (SEQ ID NO: 3)
TCATGGAGGGTGAGAATCCCG

BIP3':
                                         (SEQ ID NO: 4)
TTTCACTCTCTTTTCAAAGTTC

LF:
                                         (SEQ ID NO: 5)
CAAAGAACTGACACCCTCGC

LB:
                                         (SEQ ID NO: 6)
CAAGTACAGTGATGGAAAGATG

F3:
                                         (SEQ ID NO: 7)
GGAGAGTACCACTTTGGGACTG

B3:
                                         (SEQ ID NO: 8)
CCTTCCCTTTCAACAATTTCAC

PCR outer forward (POF):
                                         (SEQ ID NO: 9)
TAGGGTTACCCGCTGAACTT PCR outer backward (POB):
                                         (SEQ ID NO: 10)
GCGCAAAACACCATGTCTGA
```

Figure 2:
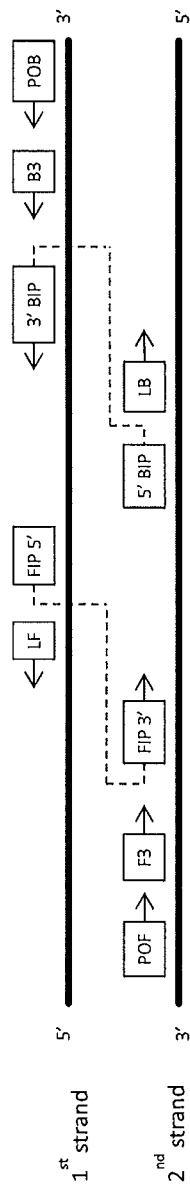
FIG. 2 shows the primer design of the primers used in Example 2. Arrows show the direction of primer extension DNA synthesis. The first L-primer FIP (primer (c) according to the invention) comprises the two parts FIP 3' (part c1) and FIP 5' (part c2). The second L-primer BIP (primer (d) according to the invention) comprises the two parts BIP 3' (part d1) and BIP 5' (part d2). The primers LF and LB are the optional primers (e) and (f) according to the invention. Primers F3 and B3 are the displacement primers essential to conventional isothermal loop-mediated amplification. Primers POF and POB are outer primers used in Example 2 for PCR.

FIG. 2 shows the positions of the primers used in the assays.

The template samples were assayed as single step or two step assays as follows;

Parenthesis shows primers and concentration of same included in the given reaction.
Conventional Single Step
qPCR (0.4 µM F3; 0.4 µM B3)
LAMP (1.6 µM FIP; 1.6 µM BIP; 0.8 µM LF; 0.8 µM LB; 0.2 µM F3; 0.2 µM B3)
Control Single Step
LAMP (1.6 µM FIP; 1.6 µM BIP)
Conventional Two Step
PCR outer (0.4 µM POF; 0.4 µM POB) followed by qPCR (0.4 µM F3; 0.4 µM B3)
Two Step According to the Invention
PCR outer (0.4 µM POF; 0.4 µM POB) followed by LAMP (1.6 µM FIP; 1.6 µM BIP;
0.8 µM LF; 0.8 µM LB; 0.2 µM F3; 0.2 µM B3)
PCR F3/B3 (0.4 µM F3; 0.4 µM B3) followed by LAMP (1.6 µM FIP; 1.6 µM BIP;
0.8 µM LF; 0.8 µM LB; 0.2 µM F3; 0.2 µM B3)
PCR FIP/BIP (0.4 µM FIP; 0.4 µM BIP) followed by LAMP (1.6 µM FIP; 1.6 µM BIP)
PCR FIP/BIP (0.4 µM FIP; 0.4 µM BIP) followed by LAMP (1.6 µM FIP; 1.6 µM BIP; 0.8 µM LF; 0.8 µM LB)
PCR FIP3'/BIP3' (0.4 µM FIP3', 0.4 µM BIP3') followed by LAMP (1.6 µM FIP, 1.6 µM BIP, 0.8 µM LF, 0.8 µM LB)

qPCR reactions were performed using the Brilliant III Ultra fast SYBR® GREEN QPCR master mix (Agilent Technologies) according to the manufacturer's instructions, primers were included as specified in the list above and 2 µL of purified DNA from *Candida glabrata* or H$_2$O for NTC. Using a thermocycler (7500 fast real-time PCR machine from Applied Biosystems), the qPCR reagent mixture was subjected to an initial 3 min at 95° C., followed by 40 thermocycles of 5 seconds at 95° C. and 20 seconds at 60° C. The device measured the development in fluorescent signal in real-time and the associated software calculated the $C_T$ value corresponding to which cycle the PCR product was detectable. $C_T$ values were converted to a detection time by taking into account the hot-start time, thermocycle times and the heating and cooling times.

PCR reactions, PCR outer, PCR F3/B3 and PCR FIP/BIP and PCR FIP3'/BIP5' were performed as follows. PCR reagent mixture (20 µL) consisted of: 2 µL, purified DNA from *Candida glabrata* or H$_2$O for no template control, 10 µl of 2× Mastermix TrueHOT (VWR) and primers as specified in the list above. Using a thermocycler, the PCR reagent mixture was subjected to an initial hot-start of 15 minutes at 95° C. followed by 12 or 15 thermocycles as specified in Table 1 and Table 2, of 30 seconds at 95° C., 30 seconds at 60° C. and 45 seconds at 72° C., final elongation was performed for 5 minutes at 72° C.

LAMP reactions were performed as follows; LAMP reaction mixture (25 µL) consisted of: 15 µL of Isothermal Mastermix (Optigene); 2 µL of purified DNA from *Candida glabrata* or first-stage PCR amplified product or H$_2$O for no template control; and primers as specified in the list above. Reactions were performed at 63° C. for 70 minutes using the Genie II device from Optigene. The device measured the development in fluorescent signal in real-time. The time for detection was determined by the associated software.

Results

The results are shown in Tables 1 and 2.

TABLE 1

Table 1. Time of detection is shown for reactions performed on template of DNA which was purified from samples with different numbers of *Candida glabrata* (100,000 to 10). The values only show the time of detection and NOT the time of pre-amplification. A dash (—) indicates that no amplification has occurred in the detection reaction, i.e. negative detection. Times are shown as hour:minutes:seconds.

| Pre-amplification | Detection | 10,000 | 1,000 | 100 | 10 | NTC |
|---|---|---|---|---|---|---|
| — | qPCR (F3, B3) | 00:21:55 | 00:26:10 | 00:29:25 | 00:29:46 | — |
| — | LAMP (FIP, BIP) | — | — | — | — | — |
| — | LAMP (FIP, BIP, LF, LB, F3, B3) | 00:15:54 | 00:32:39 | — | — | — |
| PCR outer (15 cycles) | qPCR (F3, B3) | 00:14:39 | 00:17:58 | 00:23:29 | 00:23:35 | — |

TABLE 1-continued

Table 1. Time of detection is shown for reactions performed on template of DNA which was purified from samples with different numbers of *Candida glabrata* (100,000 to 10). The values only show the time of detection and NOT the time of pre-amplification. A dash (—) indicates that no amplification has occurred in the detection reaction, i.e. negative detection. Times are shown as hour:minutes:seconds.

| Pre-amplification | Detection | 10,000 | 1,000 | 100 | 10 | NTC |
|---|---|---|---|---|---|---|
| PCR outer (15 cycles) | LAMP (FIP, BIP, LF, LB, F3, B3) | 00:09:48 | 00:11:18 | 00:13:18 | 00:14:03 | — |
| PCR F3/B3 (15 cycles) | LAMP (FIP, BIP, LF, LB, F3, B3) | 00:10:19 | 00:11:49 | 00:13:19 | 00:14:34 | — |
| PCR FIP/BIP (12 cycles) | LAMP (FIP, BIP) | 00:30:44 | 00:33:59 | 00:42:59 | — | — |
| PCR FIP/BIP (12 cycles) | LAMP (FIP, BIP, LF, LB) | 00:10:58 | 00:12:43 | 00:14:13 | 00:17:43 | — |
| PCR FIP3'/BIP3' (12 cycles) | LAMP (FIP, BIP, LF, LB) | 00:14:51 | 00:16:51 | — | — | — |

TABLE 2

Table 2. Total time for assay is shown for the limit of detection (LOD) presented in Table 1.

| Pre-amplification | Detection | Time of preamp. | Time of detection | Total time | LOD |
|---|---|---|---|---|---|
| — | qPCR (F3/B3) | N/A | 00:29:46 | 00:29:46 | <10 |
| — | LAMP (FIP, BIP, LF, LB, F3, B3) | N/A | 00:32:39 | 00:32:39 | 1000 |
| PCR outer (15cycles) | qPCR (F3/B3) | 00:46:15 | 00:23:35 | 01:09:50 | <10 |
| PCR outer (15 cycles) | LAMP (FIP, BIP, LF, LB, F3, B3) | 00:46:15 | 00:14:03 | 01:00:18 | <10 |
| PCR F3/B3 (15 cycles) | LAMP (FIP, BIP, LF, LB, F3, B3) | 00:46:15 | 00:14:34 | 01:00:49 | <10 |
| PCR FIP/BIP (12 cycles) | LAMP (FIP, BIP) | 00:41:00 | 00:42:59 | 01:23:59 | 100 |
| PCR FIP/BIP (12 cycles) | LAMP (FIP, BIP, LF, LB) | 00:41:00 | 00:17:43 | 00:58:43 | <10 |
| PCR FIP3'/BIP3' (12 cycles) | LAMP (FIP, BIP, LF, LB) | 00:41:00 | 00:16:51 | 00:57:51 | 1000 |

N/A = not applicable.
Hands on times are not included.
Times are shown as hour:minutes:seconds.

The results show the following:
- In a single step assay, qPCR is more sensitive than LAMP. LOD for qPCR is 10, LOD for LAMP is 1000. In a two-step assay, using PCR pre-amplification followed by LAMP according to the invention, LOD is increased from 1,000 to 10, i.e. comparable to qPCR
- LOD and detection times are very similar when using PCR pre-amplification with outer primers (01:00:18), PCR pre-amplification with F3/B3 primers (01:00:49) or using PCR pre-amplification with FIP/BIP primers (00:58:43) in the first step, according to the invention
- A PCR/LAMP procedure according to the invention (PCR outer, PCR F3/B3 or PCR FIP/BIP followed by LAMP) shows the same LOD as Nested PCR (PCR outer+ qPCR), but 9-11 minutes faster detection (01:09:50 compared to 01:00:18/01:00:49/00:58:43)
- The use of 12 cycles as opposed to 15 cycles of PCR pre-amplification may explain the slightly longer detection times observed for PCR FIP/BIP+LAMP (FIP, BIP, LF, LB) samples compared to PCR outer or PCR F3/B3 followed by LAMP (FIP, BIP, LF, LB, F3, B3)
- Loop primers (LF and LB) improve the LOD and accelerate the detection time in the combined PCR/LAMP according to the invention. LAMP using FIP/BIP detects 100 copies with a detection time of 00:42:39. LAMP using FIP/BIP/LF/LB detects 10 copies with a detection time of 00:17:43
- Using FIP3'/BIP3' primer set compared to FIP/BIP primer set for PCR pre-amplification results in a higher LOD (1,000 compared to 10) and slower time for detection.

Example 3

The objective of Example 3 was to investigate the possibility of isothermal detection of low copy numbers of target sequences of 5 representative organisms commonly involved in sepsis using a combination of PCR pre-amplification and LAMP amplification and detection according to the invention. The organisms include gram negative bacteria, gram positive bacteria and yeast. Furthermore the MRSA resistance marker was included.

Organisms and the specific strains detected are shown in Table 3.

TABLE 3

Table 3.

| Organism | Type | Strain |
|---|---|---|
| *Pseudomonas aeruginosa* | Gram negative | DSM 50071 |
| *Staphylococcus aureus* | Gram positive | DSM 6148 |
| *Staphylococcus aureus* | Gram positive | ATCC BAA-42 |
| *Candida albicans* | Yeast | DSM 6569 |
| *Candida glabrata* | Yeast | DSM 11226 |

Sepsis relevant organisms included in the study

Preparation of Cells
Culturing

For each organism (strain), 50 mL Falcon tubes were prepared with 10 mL of Tryptone Soya Broth (TSB) and 0.5 mL of the suspension strain (from −80° C.). Tubes were incubated at 37° C. for 24 hours±2 hours.

Checking Growth

Cell density was checked all strains using DAPI microscopy. DAPI microscopy applies a known volume of cell suspension onto a filter which is fluorescently stained with DAPI. The method stains double stranded DNA from living and dead cells and can thereby be used to determine the total number of cells that are present in the cell suspension.

Dilution Series

For each of the tubes with determined cell density, a dilution series was made from 10⁸ to 10¹ cells/mL using Peptone Salt Solution (SPO) as dilution medium. For each organism, cultivation, extraction of DNA and DAPI microscopy was performed on 10⁹/10⁸, 10⁷ and 10⁴ cells/mL.

Colony Forming Units

From each cell suspension 2×1 mL were transferred to petri dishes. Tryptone Soya Agar (TSA) (15-20 mL) was added to each of the bacterial strains and Yeast Extract Agar (depth seed) (15-20 mL) was added to each of the yeast strains. The plates were incubated at 37° C. for 24 hours±2 hours and colony forming units were determined.

DNA Extraction and Purification

DNA extractions were performed on 5 mL of cell suspension from each dilution of 10⁸ to 10¹ cells/mL. The cell suspensions were bead heated and subsequently purified by binding of DNA to silica in presence of chaotropic salts. Elution was performed in 100 µL elution buffer and stored at −20° C. until further processing.

Pre-Amplification (PCR)

Pre-amplification was performed using PCR reactions as follows: PCR reagent mixture (20 µL) consisted of: 2 µL purified DNA from DNA eluates corresponding to 100,000, 10,000, 1,000, 100, 10 cells or H₂O for no template control, 10 µl of 2× Mastermix TrueHOT (VWR) and 0.4 µM of PCR outer forward (POF) primer or PCR outer backward (POC) primer, respectively, as specified in Table 4. Reactions were performed as singleplex for amplification of the target sequence from a single specific organism using only one set of POF and POB primers or as multiplex with POF and POB primers included for simultaneous amplification of all organisms. PCR reagent mixtures were subjected to thermocycling with an initial hotstart of 15 minutes at 95° C. followed by 15 thermocycles of: 30 seconds at 95° C., 30 seconds at 60° C. and 45 seconds at 72° C. Final elongation was performed for 5 min at 72° C. Total time for pre-amplification, including hotstart and final elongation was 46 minutes 15 seconds.

Detection (LAMP)

LAMP reactions were run on the Genie II device from Optigene with real-time fluorescent detection. LAMP reactions were performed as follows (25 µL per reaction): 15 µL of Isothermal mastermix (Optigene); 2 µL of purified DNA or PCR pre-amplification product or H₂O for no template control (NTC) and primers for detection of a specific targets, 1.6 µM FIP; 1.6 µM BIP; 0.8 LF; 0.8 µM LB; 0.2 µM F3; 0.2 µM B3, see Table 4 for primer sequences. Reactions were run for 60 minutes at 63° C.

TABLE 4

| Target species | Target gene | Primers | Sequence (5' to 3') | Reference |
|---|---|---|---|---|
| Pseudomonas aeruginosa | oprL | POF | AGAAGTCGTTATGCCCAAGC (SEQ ID NO: 17) | |
| | | POB | CTGGTAGCGTTCCAGGCTTT (SEQ ID NO: 18) | |
| | | FIP | GTTGTCACCCCACCTCCGGGCGGCAAC GTTCCTCC (SEQ ID NO: 11) | Goto 2010 |
| | | BIP | CTCCGTGCAGGGCGAACTGCAGGCGAG CCAACTC (SEQ ID NO: 12) | Goto 2010 |
| | | F3 | GCGTTGCCGCCAACAATG (SEQ ID NO: 15) | Goto 2010 |
| | | B3 | GGATCTGGTTCTGCTGCT (SEQ ID NO: 16) | |
| | | LF | ACCTGCCGTGCCATACC (SEQ ID NO: 13) | Goto 2010 |
| | | LB | GTTCATGCAGCTCCAGCAG (SEQ ID NO: 14) | Goto 2010 |
| Staphylococcus aureus | femB | POF | GGTCGCGAGAAAAATGATGC (SEQ ID NO: 25) | |
| | | POB | AGCACGCTCTTCAGTTTCAC (SEQ ID NO: 26) | |
| | | FIP | TACCTTCAAGGTTTAATACGCCCATCAT CATGGCTTTACAACTGAG (SEQ ID NO: 19) | Hanaki 2011 |
| | | BIP | ACACCCGAAACATTGAAAAAGACACTTTA ACACCATAGTTTATCGCTT (SEQ ID NO: 20) | Hanaki 2011 |
| | | F3 | TGTTTAAATCACATGGTTACGAG (SEQ ID NO: 23) | Hanaki 2011 |
| | | B3 | TCACGTTCAAGGAATCTGA (SEQ ID NO: 24) | Hanaki 2011 |
| | | LF | CCATCGTACTTGGCTCGATG (SEQ ID NO: 21) | |
| | | LB | TGATAGTCAACGTAAACGTAAT (SEQ ID NO: 22) | |
| Resistance marker | mecA | POF | ACAGAAAGTCGTAACTATCCTC (SEQ ID NO: 33) | |
| | | POB | GCAGTACCTGAGCCATAATC (SEQ ID NO: 34) | |
| | | FIP | TCCCTTTTTACCAATAACTGCATCATAT GTTGGTCCCATTAACTCT (SEQ ID NO: 27) | Hanaki 2011 |

TABLE 4-continued

| Target species | Target gene | Primers | Sequence (5' to 3') | Reference |
|---|---|---|---|---|
| | | BIP | AAGCTCCAACATGAAGATGGCCGATTGT ATTGCTATTATCGTCAA (SEQ ID NO: 28) | Hanaki 2011 |
| | | F3 | GCGACTTCACATCTATTAGGT (SEQ ID NO: 31) | Hanaki 2011 |
| | | B3 | GCCATCTTTTTTCTTTTTCTCT (SEQ ID NO: 32) | Hanaki 2011 |
| | | LF | TAGCCTTTATATTCTTTTTGTT (SEQ ID NO: 29) | |
| | | LB | TATCGTGTCACAATCG (SEQ ID NO: 30) | |
| Candida albicans | 26S rRNA | POF | TAGGACTACCCGCTGAACTT (SEQ ID NO: 41) | |
| | | POB | CGAGAGAGCAGCATGCAAAA (SEQ ID NO: 42) | |
| | | FIP | CTGCATTCCCAAACAACTCGACTCACAG AGGGTGAGAATCCCG (SEQ ID NO: 35) | Inacio 2008 |
| | | BIP | TATTGGCGAGAGACCGATAGCGTTTCAC TCTCTTTTCAAAGTTC (SEQ ID NO: 36) | Inacio 2008 |
| | | F3 | GCATATCAATAAGCGGAGGAAAAG (SEQ ID NO: 39 | Inacio 2008 |
| | | B3 | CCTTCCCTTTCAACAATTTCAC (SEQ ID NO: 40) | Inacio 2008 |
| | | LF | TCKTCGAAGGAACTTTACA (SEQ ID NO: 37) | |
| | | LB | CAAGTACAGTGATGGAAAGATG (SEQ ID NO: 38) | |
| Candida glabrata | 26S rRNA | POF | TAGGGTTACCCGCTGAACTT (SEQ ID NO: 49) | |
| | | POB | GCGCAAAACACCATGTCTGA (SEQ ID NO: 50) | |
| | | FIP | CTGCATTCCCAAACAACTCGACTCATGG AGGGTGAGAATCCCG (SEQ ID NO: 43) | |
| | | BIP | TACAGGCGAGAGACCGATAGCGTTTCAC TCTCTTTTCAAAGTTC (SEQ ID NO: 44) | |
| | | F3 | GGAGAGTACCACTTTGGGACTG (SEQ ID NO: 47) | |
| | | B3 | CCTTCCCTTTCAACAATTTCAC (SEQ ID NO: 48) | Inacio 2008 |
| | | LF | CAAAGAACTGACACCCTCGC (SEQ ID NO: 45) | |
| | | LB | CAAGTACAGTGATGGAAAGATG (SEQ ID NO: 46) | |

Table 4. List of primers used for the detection of a specific target. Sequence letter K indicates G or T.
References show if primer sequences have been published or if they were designed, indicated by a blank; Goto 2010 = Goto, M. et al., J. Microbiol. Methods, 2010, 81, 247-52; Hanaki 2011 = Hanaki, K.-I. et al., J. Microbiol. Methods, 2011, 84, 251-254; Inacio 2008 = Inácio, J. et al., J. Clin. Microbiol., 2008, 46, 713-720.

Limit of Detection

Fluorescent LAMP reactions were used to detect the presence of specific organism DNA in purified DNA samples or on pre-amplification products. Table 5 shows the impact of implementing pre-amplification in the assay, illustrated through limit of detection (LOD) experiments performed on purified DNA from Candida glabrata and on pre-amplification products of the same DNA. When using pre-amplification, the LOD was decreased more than 100 fold to 10 Candida glabrata.

TABLE 5

Table 5. Illustration of limit of detection (LOD) for LAMP targeting Candida glabrata with or without PCR preamplification. Fluorescence versus time (hour:minutes:seconds) is shown.

| | Copy | Time of detection | |
|---|---|---|---|
| Target species | number | No pre-amplification | Preamplification |
| Candida glabrata | 100,000 | 00:12:54 | 00:07:48 |
| Candida glabrata | 10,000 | 00:15:54 | 00:09:48 |
| Candida glabrata | 1,000 | 00:32:39 | 00:11:18 |
| Candida glabrata | 100 | no amplification | 00:13:18 |

TABLE 5-continued

Table 5. Illustration of limit of detection (LOD) for LAMP targeting
Candida glabrata with or without PCR preamplification. Fluorescence
versus time (hour:minutes:seconds) is shown.

|  | Copy | Time of detection | |
|---|---|---|---|
| Target species | number | No pre-amplification | Preamplification |
| Candida glabrata | 10 | no amplification | 00:14:03 |
| NTC | 0 | no amplification | no amplification |

Similar experiments were performed for each target and their corresponding dilution series and are summarized in Table 6. Table 6 shows that PCR pre-amplification is required to obtain LOD of <1000 copies. Using pre-amplification LOD of 10 was observed for 4 of 5 tested organisms and 100 for the 5$^{th}$.

TABLE 6

Table 6.

| | Pre-amplification | | | |
|---|---|---|---|---|
| | − | | + | |
| Target species (primer set) | LOD | Time | LOD | Time |
| P. aeruginosa | 1,000 | 00:39:54 | <10 | 00:18:51 |
| S. aureus: MSSA (femB) | 1,000 | 00:16:53 | <10 | 00:11:59 |
| S. aureus: MRSA (mecA) | 10,000 | 00:17:29 | 100 | 00:15:23 |
| C. albicans | 1,000 | 00:19:56 | <10 | 00:19:27 |
| C. glabrata | 1,000 | 00:32:39 | <10 | 00:14:03 |

Limit of detection (LOD) and time of detection (time) in the LAMP reaction shown as hours:minutes:seconds.
Pre-amplification times were 46 minutes 15 seconds and have not been included in the detection times.
LOD of <10 indicates that the sample with the lowest tested copy number (10) was detected successfully.

Detecting Multiple Organisms

The presence of multiple organisms is known to occur in clinical samples. In this regard, it was investigated whether the assay was able to detect and distinguish presence of more than one organism in a sample. This was achieved by using multiplex pre-amplification with all five primer sets on pooled DNA eluates from different organisms. The multiplex pre-amplification products were divided into sub-samples, each of which was subjected to LAMP amplification targeting different target sequences with simultaneous real-time detection.

Table 7 shows the simultaneous detection of DNA from one or more organisms through use of multiple LAMP reactions. Purified DNA from a human blood sample was included in the study to illustrate the effect of a complex DNA source on time of detection.

TABLE 7

Table 7. Simultaneous detection of multiple targets. LAMP detection was
performed on products from multiplex PCR pre-amplification on DNA eluates
from one or more organisms (1,000 copies). Human: purified DNA from human
whole blood sample. (+) shows positive detection indicated with time
for detection as minutes:seconds. (−) shows a negative detection.

| | DNA from organisms included in sample: | | LAMP reactions with primers sets for: | | | |
|---|---|---|---|---|---|---|
| No | Organism 1 | Organism 2 | oprL | femB | mecA | C. albicans |
| 1 | P. aeruginosa | | + (13:31) | − | − | − |
| 2 | MRSA | | − | + (10:19) | + (14:31) | − |
| 3 | MSSA | | − | + (9:29) | − | − |
| 4 | C. albicans | | − | − | − | + (14:23) |
| 5 | C. glabrata | | − | − | − | − |
| 6 | P. aeruginosa | Human | + (13:16) | − | − | − |
| 7 | MRSA | Human | − | + (14:19) | + (18:16) | − |
| 8 | MSSA | Human | − | + (9:44) | − | − |
| 9 | C. albicans | Human | − | − | − | + (15:08) |
| 10 | C. glabrata | Human | − | − | − | − |
| 11 | P. aeruginosa | MRSA | + (13:31) | + (9:59) | + (13:58) | − |
| 12 | P. aeruginosa | MSSA | + (14:01) | + (9:44) | − | − |
| 13 | P. aeruginosa | C. albicans | + (13:46) | − | − | + (11:37) |
| 14 | P. aeruginosa | C. glabrata | + (13:31) | − | − | − |
| 15 | MRSA | MSSA | − | + (9:29) | + (13:28) | − |
| 16 | MRSA | C. albicans | − | + (10:28) | + (15:01) | + (14:08) |
| 17 | MRSA | C. glabrata | − | + (10:58) | + (16:44) | − |
| 18 | MSSA | C. albicans | − | + (9:59) | − | + (11:37) |
| 19 | MSSA | C. glabrata | − | + (9:44) | − | − |
| 20 | C. albicans | C. glabrata | − | − | − | + (14:45) |
| 21 | NTC | Human | − | − | − | − |
| 22 | NTC | | − | − | − | − |

Conclusion

The detection of 5 sepsis relevant organisms has been shown by use of DNA extraction and purification, pre-amplification and fluorescent LAMP detection. The results showed a decrease in the limit of detection when using pre-amplification of a factor of at least 100 in all cases. Using pre-amplification, results showed a limit of detection of <10 copies for 4 of the 5 organisms and 100 copies for 5th organism. The assay showed correct and simultaneous detection of multiple organisms. Furthermore, samples that were positive or negative for MRSA were always called correctly.

The results demonstrated the possibility of multiplex detection of target sequences present in very low copy numbers in samples comprising complex mixtures of DNA. By use of pre-amplification, the sample may be divided into multiple detection chambers or tubes without loss of sensitivity.

Example 4

RT-isoPCR was used for simultaneous multiplex detection of 24 targets, 23 mRNA targets involved in CAD and one positive control. RNA was purified from whole blood using the QIAamp RNA blood mini kit according to the manufacturer's instruction. Sample size corresponded to 22.5 uL whole blood.

Materials and Methods

Primers were designed for targeting the 23 genes listed in table 8 using a LAMP designer program. The relevant genes were chosen based on data from Elashoff et al. "Development of a blood-based gene expression algorithm for assessment of obstructive coronary artery disease in non-diabetic patients", BMC Medical Genomics 2011, 4:26. The program designed FIP, BIP, LF, LB primers for each target. The HuPO gene was included as positive control as it is highly and consistently expressed in whole blood.

TABLE 8

Primer sequences

| No | Target | FIP | BIP | LF | LB |
|---|---|---|---|---|---|
| 1 | RPL28 | CCTACGCTCACTCACCATGCGCAGGTGTCTCAGTGTTC (SEQ ID NO: 51) | GCCCAAAGTTGTGCAGAGCTGAACAGAGGATGCCTCA (SEQ ID NO: 52) | ACTGGACTAAGAGCTGGAGA (SEQ ID NO: 53) | CCACAGCAGCAGAGACTC (SEQ ID NO: 54) |
| 2 | TMC8 | GTGACCAGGAAGGCGAAGGGCTGTACAAGCTGAGTATCTT (SEQ ID NO: 55) | GGTTCTCAGGCCGGTTCTGCACGATGTCCAGCACATT (SEQ ID NO: 56) | CACGGTGAGGAGGAAGTTG (SEQ ID NO: 57) | CTGGAACGGGAGGAGTTC (SEQ ID NO: 58) |
| 3 | CD3D | TCCTCCAAGGTGGCTGTACTCTCTGTTGAGGAATGACCAG (SEQ ID NO: 59) | AACTGGGCTCGGAACAAGTGACAGTTGGTAATGGCTGC (SEQ ID NO: 60) | GCATCATCTCGATCTCGGAG (SEQ ID NO: 61) | CCTGAGACTGGTGGCTTC (SEQ ID NO: 62) |
| 4 | CD79B | CCAGCAGCAGGAAGATAGGCCACGCTGAAGGATGGTATC (SEQ ID NO: 63) | GGCTGGCATGGAGGAAGATCAGCGTCACTATGTCCTCATA (SEQ ID NO: 64) | AGCAGCGTCTGGATCATG (SEQ ID NO: 65) | TGGACATTGACCAGACAGC (SEQ ID NO: 66) |
| 5 | SPIB | TACAGGTGTGAGCCATTGCCCACTGTAGCACTTGGTGG (SEQ ID NO: 67) | AGCACTTTGGGAGGCGAGCCAGGCTGGTCTTGAATG (SEQ ID NO: 68) | TGATGGCCTGCTGTTAATGT (SEQ ID NO: 69) | GGGAATGGCTTGAACCCA (SEQ ID NO: 70) |
| 6 | HNRNPF | GCTCTGCACTGTGAACTCACTAGAGACCTCAGCTACTGTC (SEQ ID NO: 71) | GCCACTGTGTCCACATGAGGTGAGAGGAGAGAAGAAGTTGTA (SEQ ID NO: 72) | GCCGTATCTGTGGTCATACAT (SEQ ID NO: 73) | GCGACCGAGAACGACATT (SEQ ID NO: 74) |
| 7 | TFCP2 | AGCAAGCTACTTAGCCACTGTGACACTATCTGAAGTAGGTGCTA (SEQ ID NO: 75) | AGCTGGCAGGCAGTGATGAGCACTGGTGGTATGAGA (SEQ ID NO: 76) | TTTCCTCATCTTCGGTTGGG (SEQ ID NO: 77) | CTGAAATCCAAACCAGGCAATC (SEQ ID NO: 78) |
| 8 | AF289562 | AACTGCTGCTCTGCTGTCCCTGTGGATGGTTGTCAGTC (SEQ ID NO: 79) | CTCCAGGATCGGCCATGTTCAATGCAGCTTGAGGTTTCA (SEQ ID NO: 80) | TCTCATCATCTGACTCACTCCT (SEQ ID NO: 81) | ACCGCCTCTACCTGTCTC (SEQ ID NO: 82) |
| 9 | KLRC4 | CTTCCCACTGCCAAGATCCATTCTGGTGAAGTCATATCATTGGA (SEQ ID NO: 83) | GGCTCCATTCTCTCACCCAACAAGCTCGAGGCATAGAGT (SEQ ID NO: 84) | GTTGGAATGTGTACTAGTCCCA (SEQ ID NO: 85) | ATTGAAATGCAGAAGGGAGACT (SEQ ID NO: 86) |
| 10 | SLAMF7 | GGAGTGCAGTGGTGCCATGGCATGAGAATCGCTTGA (SEQ ID NO: 87) | ACACCTGTGCTAGGTCAGTCTAGATGGTGAGCTCTGTGT (SEQ ID NO: 88) | CTCAGCTCACTGCAACCT (SEQ ID NO: 89) | CGTAAGATGAACATCCCTACCA (SEQ ID NO: 90) |

TABLE 8-continued

Primer sequences

| No | Target | FIP | BIP | LF | LB |
|----|--------|-----|-----|-----|-----|
| 11 | TNFRSF10c | CACTTCCGGCACATCTCTGGACCATGACCAGAGACACA (SEQ ID NO: 91) | TAGCAGGTGCCCTAGTGGGCCAAATTCTTCAACACACTGG (SEQ ID NO: 92) | TGCCTTCTTTACACTGACACA (SEQ ID NO: 93) | AGTCAGTAATTGTACGTCCTGG (SEQ ID NO: 94) |
| 12 | CXCR2 | ATGAGTAGACGGTCCTTCGGAAATTCATATGTCTAGCATCTGG (SEQ ID NO: 95) | GTTAGCCCAGCCTGCTATGAGGATCCGTAACAGCATCCG (SEQ ID NO: 96) | CAGGAGCAAGGACAGAC (SEQ ID NO: 97) | GACATGGGCAACAATACAGC (SEQ ID NO: 98) |
| 13 | TLR4 | GTTCTCCTGGCAGTGAGAAGGTTGATGGACCTCTGAATCTCT (SEQ ID NO: 99) | ACGTGTGAAGGTATTCAAGGCAATGTGGTCAAGGAGCATTG (SEQ ID NO: 100) | CCAGCCATCTGTGTCTCC (SEQ ID NO: 101) | CATTGCTGTTTCCTGTTGGG (SEQ ID NO: 102) |
| 14 | AQP9 | ACAATGGCTCACAGATTCCTGGAAGCCACAGCCTCTAATTG (SEQ ID NO: 103) | TCATCTGGCTGTGAAAGTGAGGCTTCTCTGAGGACTCCTGT (SEQ ID NO: 104) | TCTGGTAAGAGTCTCTGACTGT (SEQ ID NO: 105) | ACCACAACAGGTAGGTATTGG (SEQ ID NO: 106) |
| 15 | S100A8 | TCCAGCTCGGTCAACATGATGCCTGCATGTCTCTTGTCAG (SEQ ID NO: 107) | ACGTCTACCACAAGTACTCCCTCAATTTCTTCAGGTCATCCCT (SEQ ID NO: 108) | CACCAGGTCTTCTGAAAGACA (SEQ ID NO: 109) | GGGAATTTCGATGCCGTCTA (SEQ ID NO: 110) |
| 16 | NCF4 | AAGCATGGAACTGGCGGTAGTCGTCATCGAGGTGAAGA (SEQ ID NO: 111) | GCCAGACAGCAAGAGCAGTCTCCTGTTTCACACCCAC (SEQ ID NO: 112) | GCGGTAGATGAGGTACTTGG (SEQ ID NO: 113) | CACACTCCCAGCCAAAGT (SEQ ID NO: 114) |
| 17 | KCNE3 | TCAGTCAGTTTCAGGAGTCCCTATGTGTCCAGAGACATCCT (SEQ ID NO: 115) | AGCAGTCTGAGCTTCTACCGAGTTCCATTGGTAGTCTCCATAG (SEQ ID NO: 116) | CACACTAAGGCTCCTCCAC (SEQ ID NO: 117) | CCCACCTCAATCCCTGTTG (SEQ ID NO: 118) |
| 18 | S100A12 | AGCGCAATGGCTACCAGGGCCTGGATGCTAATCAAGAT (SEQ ID NO: 119) | CCCATTACCACACCCACAAAGATCATTGAGGACATTGCTGG (SEQ ID NO: 120) | ATTCTTGAAAGTCGACCTGTTC (SEQ ID NO: 121) | TAGGTAGCTCTCTGAAGGCTT (SEQ ID NO: 122) |
| 19 | CLEC4E | TTCCTGCTCCTCCTGTGAGTAAGAACTGCTCAGCCATG (SEQ ID NO: 123) | GGACTGTCAGACCAGGTTGTCCTCAGAGACTTTGTCAAAGGT (SEQ ID NO: 124) | GATAACCACCAGGTGAGCC (SEQ ID NO: 125) | GAGGGTCAGTGGCAATGG (SEQ ID NO: 126) |
| 20 | CASP5 | CCTTCTCCTCGTGGATCTTGCCATCCTTGGCACTCATCTC (SEQ ID NO: 127) | AACACCACATAACGTGTCCTGGTTCTGGAAGCATGTGATGAG (SEQ ID NO: 128) | TGCCTCCAGGTTCTCAGA (SEQ ID NO: 129) | GGCTCCATCTTCATTACGGAA (SEQ ID NO: 130) |
| 21 | TNFAIP6 | CCTTAGCTTCTGCGTAGGTGAGATATGGCTTGAACGAGCAG (SEQ ID NO: 131) | TTGAAGGCGGCCATCTCGCAGCAGCACAGAGATGAA (SEQ ID NO: 132) | CCAGACCGTGCTTCTCTG (SEQ ID NO: 133) | ACTTACAAGCAGCTAGAGGC (SEQ ID NO: 134) |
| 22 | IL18RAP | CCAAGCGTCTGATCCTTGCTTCTACAGGCACTGGATTGA (SEQ ID NO: 135) | TTCCAAGTGAGGCCACTTCATCCATCAGGAAATAGGCTCAGG (SEQ ID NO: 136) | CCGGTACAGCAGCACTATT (SEQ ID NO: 137) | TCTGAGTGAAGAACACTTGGC (SEQ ID NO: 138) |

TABLE 8-continued

Primer sequences

| No | Target | FIP | BIP | LF | LB |
|---|---|---|---|---|---|
| 23 | AF161365 | ACCTCGGCCAAT GAACGGACATCT CCAACCTCACAGA (SEQ ID NO: 139) | ATAGAGTGGGA GGTGGGAGCTC TTCCTCTAGCAC AGACC (SEQ ID NO: 140) | GTACTGATC ACTTCCTGT CCTC (SEQ ID NO: 141) | CCTCGTG CTGCCTTC ATT (SEQ ID NO: 142) |
| 24 | HuPO | CGCATCATGGTG TTCTTGCCAAGCA GATGCAGCAGAT C (SEQ ID NO: 143) | CTCTGGAGAAAC TGCTGCCTCTC AGTGAGGTCCT CCTTG (SEQ ID NO: 144) | ATCAGCACC ACAGCCTTC (SEQ ID NO: 145) | GGAATGTG GGCTTTG TGTTC (SEQ ID NO: 146) |

25 x 1.5 μl RNA sample was subjected to RT-PCR. One reaction for each of the 24 target genes as well as one multiplex RT-reaction. RT-PCR was performed using one primer set FIP and BIP per target in the singleplex reactions and a pool of primer sets containing all 24 primer sets in the multiplex reaction.

RT-PCR step

The Agilent AffinityScript One-Step RT-PCR kit was used for RT-PCR.

20 or 50 uL RT-PCR reaction volumes contained:
50% Hercules II RT-PCR 2× Master Mix
Primers (final concentration of FIP: 0.4 uM; BIP: 0.4 uM)
1.5 uL sample RNA (1~100 ng)
1% AffinityScript RT/Rnase block
$H_2O$ Temperatures:
5 minutes at 45 degrees
1 minute at 95 degrees
8 thermocycles of
  20 seconds at 95 degrees
  20 seconds at 60 degrees
  30 seconds at 72 degrees
3 minutes at 72 degrees All 25 reactions were amplified simultaneously in a RT-PCR with 8 cycles. The reaction product from the multiplex RT-reaction was split in 24 subsamples.

The multiplex sample RT-PCR reaction product was subsequently divided into 24 sub samples.

1 μl RT-reaction products (or sub-sample thereof) was subjected to isothermal amplifications, performed using the Optigene Isothermal Mastermix kit.

10 uL reaction volumes containing:
6 uL isothermal mastermix
1 uL primers (final concentration of 1.6 uM FIP; 1.6 uM BIP; 0.8 uM LF; 0.8 uM LB)
1 uL PCR product or NTC
2 uL $H_2O$ Isothermal amplification was performed using one primer set (FIP, BIP, LF and LB) per target.

Time of detection (of the isothermal reaction) is shown in table 9.

TABLE 9

Time of detection (h:min:sec) for isoPCR, singleplex and various multiplex reactions, targeting the 24 genes.

| Detection | Singleplex | Multiplex 24 targets |
|---|---|---|
| RPL28 | 00:11:19 | 00:12:49 |
| TMC8 | 00:11:04 | 00:13:19 |
| CD3D | 00:09:04 | 00:11:04 |
| CD79B | 00:17:04 | 00:20:19 |
| SPIB | 00:35:25 | 00:38:55 |
| HNRNPF | 00:09:10 | 00:10:55 |
| TFCP2 | 00:12:10 | 00:14:55 |
| AF289562 | 00:09:40 | 00:11:10 |
| KLRC4 | 00:14:03 | 00:15:33 |
| SLAMF7 | 00:08:48 | 00:10:33 |
| TNFRSF10c | 00:11:03 | 00:12:33 |
| CXCR2 | 00:41:05 | 00:46:30 |
| TLR4 | 00:17:24 | 00:20:09 |
| AQP9 | 00:23:20 | 00:30:05 |
| S100A8 | 00:26:20 | 00:31:35 |
| NCF4 | 00:17:24 | 00:20:54 |
| KCNE3 | 00:27:22 | 00:35:05 |
| S100A12 | 00:10:37 | 00:12:22 |
| CLEC4E | 00:09:37 | 00:11:52 |
| CASP5 | 00:15:22 | 00:18:37 |
| TNFAIP6 | 00:18:55 | 00:23:35 |
| IL18RAP | 00:10:10 | 00:13:10 |
| AF161365 | 00:09:25 | 00:11:40 |
| HuPO | 00:10:57 | 00:13:12 |

Melting temperature analysis was performed on all samples immediately following isothermal amplification. The correct identity of the detected target in the multiplex reaction setup was confirmed.

As expected for all 24 targets, the time of detection is slightly increased when performing isoPCR in multiplex compared to singleplex reactions.

However, it was demonstrated to be possible to correctly identify the presence of 24 target RNA sequences in 1.5 μl RNA sample (derived from a 22.5 μl blood sample) in a single multiplex isoPCR procedure in less than 1 hour.

The invention claimed is:

1. A method for detecting the presence or absence of two or more target nucleic acid sequences in a sample, the method comprising the steps of:
   (a) providing a sample;
   (b) optionally extracting nucleic acid sequences from the sample, thereby providing a nucleic acid extract sample;
   (c) providing, for each target nucleic acid sequence, a pair of nucleic acid primers, said pair of primers comprising a primer (a) having a 3' part that is substantially complementary to a part of the target sequence, the presence or absence of which is to be detected, or a sequence downstream (3') thereof, and a primer (b) having a 3' part that is substantially homologous to a part of the target sequence, the presence or absence of which is to be detected, or a sequence upstream (5') thereof, the pair of nucleic acid primers being suitable for use in a polymerase chain reaction (PCR)-mediated amplification of a nucleic acid sequence comprising the target nucleic acid sequence;
   (d) providing, for each target nucleic acid sequence, a pair of nucleic acid primers, said pair of primers comprising a primer (c) having a 3' part (c1) that is substantially complementary to a first part of the target sequence, the presence or absence of which is to be detected, and a 5' part (c2) that is substantially homologous to a second part of the target sequence, said second part of the target nucleic acid sequence being located upstream (5') of the first part of the target sequence, and a primer (d) comprising a 3' part (d1) that is substantially homologous to a fourth part of the target sequence, the presence or absence of which is to be detected, and a 5' part (d2) that is substantially complementary to a third part of the target sequence, said third part being located upstream (5') of the second part, and said fourth part being located upstream (5') of the third part of the target nucleic acid sequence, the pair of nucleic acid primers (c) and (d) being suitable for use in a loop-mediated amplification (LAMP) reaction for amplifying the target nucleic acid sequence;
   (e) optionally providing, for each target nucleic acid sequence, one or more nucleic acid primers e) and f), the primer e) having a sequence that is substantially homologous to a fifth part of the target sequence, said fifth part being located upstream (5') of the first part and downstream (3') of the second part of the target nucleic acid sequence, the primer f) having a sequence that is substantially complementary to a sixth part of the target sequence, said sixth part being located upstream (5') of the third part, and downstream (3') of the fourth part of the target nucleic acid sequence;
   (f) providing a pre-amplified sample pre-amplified with the primers (a) and (b) provided in step (c), wherein the amount of the two or more target nucleic acid sequences in the sample is increased in a multiplex PCR-mediated amplification, wherein the pre-amplified sample is divided into two or more subsamples;
   (g) subjecting the two or more pre-amplified subsamples of step (f), or a subsample thereof, to a loop-mediated amplification (LAMP) reaction, using pairs of nucleic acid primers provided in step (d), and optionally, one or more primers provided in step (e), thereby providing sample reaction products; and
   (h) detecting the presence or absence of a nucleic acid amplification product in the sample reaction products of step (g).

2. The method according to claim 1 for detecting the presence or absence of five or more different target nucleic acid sequences in a sample, the method comprising an additional step of dividing the pre-amplified sample of step (f) into five or more subsamples and subjecting the five or more subsamples to the process of steps (g) and (h).

3. The method according to claim 2, wherein each of the pairs of primers a) and b) provided in step (c) has substantially the same melting point.

4. The method according to claim 1, wherein the fifth part of the target nucleic acid sequences does not comprise parts of the first and the second part of the target sequences, and wherein the sixth part of the target nucleic acid sequences does not comprise parts of the third and the fourth part of the target nucleic acid sequences.

5. The method according to claim 1, wherein the fifth part of the target nucleic acid sequences comprises parts of the first and parts of the second part of the target sequences, and wherein the sixth part of the target nucleic acid sequences comprises parts of the third and parts of the fourth part of the target nucleic acid sequences.

6. The method according to claim 5, wherein the fifth part of the target nucleic acid sequences consists of parts of the first and parts of the second part of the target sequences, and wherein the sixth part of the target nucleic acid sequences consists of parts of the third and parts of the fourth part of the target nucleic acid sequences.

7. The method according to claim 1, wherein the nucleic acid primer a) provided in step (c) comprises a 3' part that is substantially identical to the 3' part of the nucleic acid primer c) provided in step (d), and wherein the nucleic acid primer b) provided in step (c) comprises a 3' part that is substantially identical to the 3' part of the nucleic acid primer d) provided in step (d).

8. The method according to claim 7, wherein the nucleic acid primer a) provided in step (c) is substantially identical to the 3' part of the nucleic acid primer c) provided in step (d), and wherein the nucleic acid primer b) provided in step (c) is substantially identical to the 3' part of the nucleic acid primer d) provided in step (d).

9. The method according to claim 7, wherein the nucleic acid primer a) provided in step (c) is substantially identical to the nucleic acid primer c) provided in step (d), and wherein the nucleic acid primer b) provided in step (c) is substantially identical to the nucleic acid primer d) provided in step (d).

10. The method according to claim 1, wherein the nucleic acid primers e) and f) are provided in step (e) and used in step (g).

11. The method according to claim 10, wherein one or both of the nucleic acid primers c) and d) provided in step (d) comprises a central linker sequence between the 3' and the 5' part, consisting of at least 4 nucleotides, wherein the central linker sequence is not complementary or homologous to the target sequence.

12. The method according to claim 1, wherein the sample is a blood sample.

13. The method according to claim 1, wherein the multiplex PCR-mediated amplification in step (f) proceeds with between 10 and 15 PCR cycles.

* * * * *

SEQUENCE LISTING

<160> NUMBER OF SEQ ID NOS: 146

<210> SEQ ID NO 1
<211> LENGTH: 43
<212> TYPE: DNA

```
<213> ORGANISM: Artificial Sequence
<220> FEATURE:
<223> OTHER INFORMATION: Primer

<400> SEQUENCE: 1
ctgcattccc aaacaactcg actcatggag ggtgagaatc ccg                    43

<210> SEQ ID NO 2
<211> LENGTH: 44
<212> TYPE: DNA
<213> ORGANISM: Artificial Sequence
<220> FEATURE:
<223> OTHER INFORMATION: Primer

<400> SEQUENCE: 2
tacaggcgag agaccgatag cgtttcactc tcttttcaaa gttc                   44

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
tcatggaggg tgagaatccc g                                            21

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
tttcactctc ttttcaaagt tc                                           22

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
caaagaactg acaccctcgc                                              20

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
caagtacagt gatggaaaga tg                                           22

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
ggagagtacc actttgggac tg                                           22
```

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ccttcccttt caacaatttc ac                                        22

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tagggttacc cgctgaactt                                           20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gcgcaaaaca ccatgtctga                                           20

<210> SEQ ID NO 11
<211> LENGTH: 35
<212> TYPE: DNA
<213> ORGANISM: Artificial Sequence
<220> FEATURE:
<223> OTHER INFORMATION: Primer

<400> SEQUENCE: 11
gttgtcaccc cacctccggg cggcaacgtt cctcc                          35

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
ctccgtgcag ggcgaactgc aggcgagcca actc                           34

<210> SEQ ID NO 13
<211> LENGTH: 17
<212> TYPE: DNA
<213> ORGANISM: Artificial Sequence
<220> FEATURE:
<223> OTHER INFORMATION: Primer

<400> SEQUENCE: 13
acctgccgtg ccatacc                                              17

<210> SEQ ID NO 14
<211> LENGTH: 19
<212> TYPE: DNA
<213> ORGANISM: Artificial Sequence
<220> FEATURE:

<223> OTHER INFORMATION: Primer

<400> SEQUENCE: 14
gttcatgcag ctccagcag                                                    19

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
gcgttgccgc caacaatg                                                     18

<210> SEQ ID NO 16
<211> LENGTH: 18
<212> TYPE: DNA
<213> ORGANISM: Artificial Sequence
<220> FEATURE:
<223> OTHER INFORMATION: Primer

<400> SEQUENCE: 16
ggatctggtt ctgctgct                                                     18

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
agaagtcgtt atgcccaagc                                                   20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ctggtagcgt tccaggcttt                                                   20

<210> SEQ ID NO 19
<211> LENGTH: 46
<212> TYPE: DNA
<213> ORGANISM: Artificial Sequence
<220> FEATURE:
<223> OTHER INFORMATION: Primer

<400> SEQUENCE: 19
taccttcaag gtttaatacg cccatcatca tggctttaca actgag                      46

<210> SEQ ID NO 20
<211> LENGTH: 48
<212> TYPE: DNA
<213> ORGANISM: Artificial Sequence
<220> FEATURE:
<223> OTHER INFORMATION: Primer

<400> SEQUENCE: 20
acacccgaaa cattgaaaaa gacactttaa caccatagtt tatcgctt                    48

```
<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
ccatcgtact tggctcgatg                                                   20

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
tgatagtcaa cgtaaacgta at                                                22

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
tgtttaaatc acatggttac gag                                               23

<210> SEQ ID NO 24
<211> LENGTH: 19
<212> TYPE: DNA
<213> ORGANISM: Artificial Sequence
<220> FEATURE:
<223> OTHER INFORMATION: Primer

<400> SEQUENCE: 24
tcacgttcaa ggaatctga                                                    19

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
ggtcgcgaga aaaatgatgc                                                   20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
agcacgctct tcagtttcac                                                   20

<210> SEQ ID NO 27
<211> LENGTH: 46
<212> TYPE: DNA
<213> ORGANISM: Artificial Sequence
<220> FEATURE:
<223> OTHER INFORMATION: Primer
```

```
<400> SEQUENCE: 27
tcccttttta ccaataactg catcatatgt tggtcccatt aactct                    46

<210> SEQ ID NO 28
<211> LENGTH: 45
<212> TYPE: DNA
<213> ORGANISM: Artificial Sequence
<220> FEATURE:
<223> OTHER INFORMATION: Primer

<400> SEQUENCE: 28
aagctccaac atgaagatgg ccgattgtat tgctattatc gtcaa                     45

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
tagcctttat attcttttg tt                                               22

<210> SEQ ID NO 30
<211> LENGTH: 16
<212> TYPE: DNA
<213> ORGANISM: Artificial Sequence
<220> FEATURE:
<223> OTHER INFORMATION: Primer

<400> SEQUENCE: 30
tatcgtgtca caatcg                                                     16

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
gcgacttcac atctattagg t                                               21

<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
gccatctttt ttctttttct ct                                              22

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
acagaaagtc gtaactatcc tc                                              22

<210> SEQ ID NO 34
<211> LENGTH: 20
```

```
<212> TYPE: DNA
<213> ORGANISM: Artificial Sequence
<220> FEATURE:
<223> OTHER INFORMATION: Primer

<400> SEQUENCE: 34
gcagtacctg agccataatc                                                    20

<210> SEQ ID NO 35
<211> LENGTH: 43
<212> TYPE: DNA
<213> ORGANISM: Artificial Sequence
<220> FEATURE:
<223> OTHER INFORMATION: Primer

<400> SEQUENCE: 35
ctgcattccc aaacaactcg actcacagag ggtgagaatc ccg                          43

<210> SEQ ID NO 36
<211> LENGTH: 44
<212> TYPE: DNA
<213> ORGANISM: Artificial Sequence
<220> FEATURE:
<223> OTHER INFORMATION: Primer

<400> SEQUENCE: 36
tattggcgag agaccgatag cgtttcactc tcttttcaaa gttc                         44

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
tcktcgaagg aactttaca                                                     19

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
caagtacagt gatggaaaga tg                                                 22

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
gcatatcaat aagcggagga aaag                                               24

<210> SEQ ID NO 40
<211> LENGTH: 22
<212> TYPE: DNA
<213> ORGANISM: Artificial Sequence
<220> FEATURE:
<223> OTHER INFORMATION: Primer

<400> SEQUENCE: 40
```

```
ccttcccttt caacaatttc ac                                            22

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
taggactacc cgctgaactt                                               20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
cgagagagca gcatgcaaaa                                               20

<210> SEQ ID NO 43
<211> LENGTH: 43
<212> TYPE: DNA
<213> ORGANISM: Artificial Sequence
<220> FEATURE:
<223> OTHER INFORMATION: Primer

<400> SEQUENCE: 43
ctgcattccc aaacaactcg actcatggag ggtgagaatc ccg                     43

<210> SEQ ID NO 44
<211> LENGTH: 44
<212> TYPE: DNA
<213> ORGANISM: Artificial Sequence
<220> FEATURE:
<223> OTHER INFORMATION: Primer

<400> SEQUENCE: 44
tacaggcgag agaccgatag cgtttcactc tcttttcaaa gttc                    44

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
caaagaactg acaccctcgc                                               20

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
caagtacagt gatggaaaga tg                                            22

<210> SEQ ID NO 47
<211> LENGTH: 22
<212> TYPE: DNA
<213> ORGANISM: Artificial Sequence
```

<220> FEATURE:
<223> OTHER INFORMATION: Primer

<400> SEQUENCE: 47
ggagagtacc actttgggac tg								22

<210> SEQ ID NO 48
<211> LENGTH: 22
<212> TYPE: DNA
<213> ORGANISM: Artificial Sequence
<220> FEATURE:
<223> OTHER INFORMATION: Primer

<400> SEQUENCE: 48
ccttcccttt caacaatttc ac								22

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
tagggttacc cgctgaactt								20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
gcgcaaaaca ccatgtctga								20

<210> SEQ ID NO 51
<211> LENGTH: 38
<212> TYPE: DNA
<213> ORGANISM: Artificial Sequence
<220> FEATURE:
<223> OTHER INFORMATION: Primer

<400> SEQUENCE: 51
cctacgctca ctcaccatgc gcaggtgtct cagtgttc								38

<210> SEQ ID NO 52
<211> LENGTH: 37
<212> TYPE: DNA
<213> ORGANISM: Artificial Sequence
<220> FEATURE:
<223> OTHER INFORMATION: Primer

<400> SEQUENCE: 52
gcccaaagtt gtgcagagct gaacagagga tgcctca								37

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
actggactaa gagctggaga								20

<210> SEQ ID NO 54
<211> LENGTH: 18
<212> TYPE: DNA
<213> ORGANISM: Artificial Sequence
<220> FEATURE:
<223> OTHER INFORMATION: Primer

<400> SEQUENCE: 54
ccacagcagc agagactc                                                 18

<210> SEQ ID NO 55
<211> LENGTH: 40
<212> TYPE: DNA
<213> ORGANISM: Artificial Sequence
<220> FEATURE:
<223> OTHER INFORMATION: Primer

<400> SEQUENCE: 55
gtgaccagga aggcgaaggg ctgtacaagc tgagtatctt                         40

<210> SEQ ID NO 56
<211> LENGTH: 37
<212> TYPE: DNA
<213> ORGANISM: Artificial Sequence
<220> FEATURE:
<223> OTHER INFORMATION: Primer

<400> SEQUENCE: 56
ggttctcagg ccggttctgc acgatgtcca gcacatt                            37

<210> SEQ ID NO 57
<211> LENGTH: 19
<212> TYPE: DNA
<213> ORGANISM: Artificial Sequence
<220> FEATURE:
<223> OTHER INFORMATION: Primer

<400> SEQUENCE: 57
cacggtgagg aggaagttg                                                19

<210> SEQ ID NO 58
<211> LENGTH: 18
<212> TYPE: DNA
<213> ORGANISM: Artificial Sequence
<220> FEATURE:
<223> OTHER INFORMATION: Primer

<400> SEQUENCE: 58
ctggaacggg aggagttc                                                 18

<210> SEQ ID NO 59
<211> LENGTH: 40
<212> TYPE: DNA
<213> ORGANISM: Artificial Sequence
<220> FEATURE:
<223> OTHER INFORMATION: Primer

<400> SEQUENCE: 59
tcctccaagg tggctgtact ctctgttgag gaatgaccag                         40

<210> SEQ ID NO 60
<211> LENGTH: 38
<212> TYPE: DNA
<213> ORGANISM: Artificial Sequence
<220> FEATURE:
<223> OTHER INFORMATION: Primer

<400> SEQUENCE: 60
aactgggctc ggaacaagtg acagttggta atggctgc                                  38

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
gcatcatctc gatctcggag                                                      20

<210> SEQ ID NO 62
<211> LENGTH: 18
<212> TYPE: DNA
<213> ORGANISM: Artificial Sequence
<220> FEATURE:
<223> OTHER INFORMATION: Primer

<400> SEQUENCE: 62
cctgagactg gtggcttc                                                        18

<210> SEQ ID NO 63
<211> LENGTH: 39
<212> TYPE: DNA
<213> ORGANISM: Artificial Sequence
<220> FEATURE:
<223> OTHER INFORMATION: Primer

<400> SEQUENCE: 63
ccagcagcag gaagataggc cacgctgaag gatggtatc                                 39

<210> SEQ ID NO 64
<211> LENGTH: 40
<212> TYPE: DNA
<213> ORGANISM: Artificial Sequence
<220> FEATURE:
<223> OTHER INFORMATION: Primer

<400> SEQUENCE: 64
ggctggcatg gaggaagatc agcgtcacta tgtcctcata                                40

<210> SEQ ID NO 65
<211> LENGTH: 18
<212> TYPE: DNA
<213> ORGANISM: Artificial Sequence
<220> FEATURE:
<223> OTHER INFORMATION: Primer

<400> SEQUENCE: 65
agcagcgtct ggatcatg                                                        18

<210> SEQ ID NO 66
<211> LENGTH: 19
<212> TYPE: DNA
<213> ORGANISM: Artificial Sequence
<220> FEATURE:
<223> OTHER INFORMATION: Primer

<400> SEQUENCE: 66
tggacattga ccagacagc                                                       19

<210> SEQ ID NO 67

<210> SEQ ID NO 67
<211> LENGTH: 38
<212> TYPE: DNA
<213> ORGANISM: Artificial Sequence
<220> FEATURE:
<223> OTHER INFORMATION: Primer

<400> SEQUENCE: 67
tacaggtgtg agccattgcc cactgtagca cttggtgg                         38

<210> SEQ ID NO 68
<211> LENGTH: 36
<212> TYPE: DNA
<213> ORGANISM: Artificial Sequence
<220> FEATURE:
<223> OTHER INFORMATION: Primer

<400> SEQUENCE: 68
agcactttgg gaggcgagcc aggctggtct tgaatg                           36

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
tgatggcctg ctgttaatgt                                             20

<210> SEQ ID NO 70
<211> LENGTH: 18
<212> TYPE: DNA
<213> ORGANISM: Artificial Sequence
<220> FEATURE:
<223> OTHER INFORMATION: Primer

<400> SEQUENCE: 70
gggaatggct tgaaccca                                               18

<210> SEQ ID NO 71
<211> LENGTH: 40
<212> TYPE: DNA
<213> ORGANISM: Artificial Sequence
<220> FEATURE:
<223> OTHER INFORMATION: Primer

<400> SEQUENCE: 71
gctctgcact gtgaactcac tagagacctc agctactgtc                       40

<210> SEQ ID NO 72
<211> LENGTH: 42
<212> TYPE: DNA
<213> ORGANISM: Artificial Sequence
<220> FEATURE:
<223> OTHER INFORMATION: Primer

<400> SEQUENCE: 72
gccactgtgt ccacatgagg tgagaggaga gaagaagttg ta                    42

<210> SEQ ID NO 73
<211> LENGTH: 21
<212> TYPE: DNA
<213> ORGANISM: Artificial Sequence
<220> FEATURE:
<223> OTHER INFORMATION: Primer

<400> SEQUENCE: 73
gccgtatctg tggtcataca t                                       21

<210> SEQ ID NO 74
<211> LENGTH: 18
<212> TYPE: DNA
<213> ORGANISM: Artificial Sequence
<220> FEATURE:
<223> OTHER INFORMATION: Primer

<400> SEQUENCE: 74
gcgaccgaga acgacatt                                           18

<210> SEQ ID NO 75
<211> LENGTH: 44
<212> TYPE: DNA
<213> ORGANISM: Artificial Sequence
<220> FEATURE:
<223> OTHER INFORMATION: Primer

<400> SEQUENCE: 75
agcaagctac ttagccactg tgacactatc tgaagtaggt gcta              44

<210> SEQ ID NO 76
<211> LENGTH: 36
<212> TYPE: DNA
<213> ORGANISM: Artificial Sequence
<220> FEATURE:
<223> OTHER INFORMATION: Primer

<400> SEQUENCE: 76
agctggcagg cagtgatgag cactggtggt atgaga                       36

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
tttcctcatc ttcggttggg                                         20

<210> SEQ ID NO 78
<211> LENGTH: 22
<212> TYPE: DNA
<213> ORGANISM: Artificial Sequence
<220> FEATURE:
<223> OTHER INFORMATION: Primer

<400> SEQUENCE: 78
ctgaaatcca aaccaggcaa tc                                      22

<210> SEQ ID NO 79
<211> LENGTH: 38
<212> TYPE: DNA
<213> ORGANISM: Artificial Sequence
<220> FEATURE:
<223> OTHER INFORMATION: Primer

<400> SEQUENCE: 79
aactgctgct ctgctgtccc tgtggatggt tgtcagtc                     38

<210> SEQ ID NO 80
<211> LENGTH: 39
<212> TYPE: DNA

```
<213> ORGANISM: Artificial Sequence
<220> FEATURE:
<223> OTHER INFORMATION: Primer

<400> SEQUENCE: 80
ctccaggatc ggccatgttc aatgcagctt gaggtttca                              39

<210> SEQ ID NO 81
<211> LENGTH: 22
<212> TYPE: DNA
<213> ORGANISM: Artificial Sequence
<220> FEATURE:
<223> OTHER INFORMATION: Primer

<400> SEQUENCE: 81
tctcatcatc tgactcactc ct                                               22

<210> SEQ ID NO 82
<211> LENGTH: 18
<212> TYPE: DNA
<213> ORGANISM: Artificial Sequence
<220> FEATURE:
<223> OTHER INFORMATION: Primer

<400> SEQUENCE: 82
accgcctcta cctgtctc                                                    18

<210> SEQ ID NO 83
<211> LENGTH: 44
<212> TYPE: DNA
<213> ORGANISM: Artificial Sequence
<220> FEATURE:
<223> OTHER INFORMATION: Primer

<400> SEQUENCE: 83
cttcccactg ccaagatcca ttctggtgaa gtcatatcat tgga                       44

<210> SEQ ID NO 84
<211> LENGTH: 39
<212> TYPE: DNA
<213> ORGANISM: Artificial Sequence
<220> FEATURE:
<223> OTHER INFORMATION: Primer

<400> SEQUENCE: 84
ggctccattc tctcacccaa caagctcgag gcatagagt                             39

<210> SEQ ID NO 85
<211> LENGTH: 22
<212> TYPE: DNA
<213> ORGANISM: Artificial Sequence
<220> FEATURE:
<223> OTHER INFORMATION: Primer

<400> SEQUENCE: 85
gttggaatgt gtactagtcc ca                                               22

<210> SEQ ID NO 86
<211> LENGTH: 22
<212> TYPE: DNA
<213> ORGANISM: Artificial Sequence
<220> FEATURE:
<223> OTHER INFORMATION: Primer

<400> SEQUENCE: 86
attgaaatgc agaagggaga ct                                               22
```

<210> SEQ ID NO 87
<211> LENGTH: 36
<212> TYPE: DNA
<213> ORGANISM: Artificial Sequence
<220> FEATURE:
<223> OTHER INFORMATION: Primer

<400> SEQUENCE: 87
ggagtgcagt ggtgccatgg catgagaatc gcttga                                36

<210> SEQ ID NO 88
<211> LENGTH: 39
<212> TYPE: DNA
<213> ORGANISM: Artificial Sequence
<220> FEATURE:
<223> OTHER INFORMATION: Primer

<400> SEQUENCE: 88
acacctgtgc taggtcagtc tagatggtga gctctgtgt                             39

<210> SEQ ID NO 89
<211> LENGTH: 18
<212> TYPE: DNA
<213> ORGANISM: Artificial Sequence
<220> FEATURE:
<223> OTHER INFORMATION: Primer

<400> SEQUENCE: 89
ctcagctcac tgcaacct                                                    18

<210> SEQ ID NO 90
<211> LENGTH: 22
<212> TYPE: DNA
<213> ORGANISM: Artificial Sequence
<220> FEATURE:
<223> OTHER INFORMATION: Primer

<400> SEQUENCE: 90
cgtaagatga acatccctac ca                                               22

<210> SEQ ID NO 91
<211> LENGTH: 38
<212> TYPE: DNA
<213> ORGANISM: Artificial Sequence
<220> FEATURE:
<223> OTHER INFORMATION: Primer

<400> SEQUENCE: 91
cacttccggc acatctctgg accatgacca gagacaca                              38

<210> SEQ ID NO 92
<211> LENGTH: 40
<212> TYPE: DNA
<213> ORGANISM: Artificial Sequence
<220> FEATURE:
<223> OTHER INFORMATION: Primer

<400> SEQUENCE: 92
tagcaggtgc cctagtgggc caaattcttc aacacactgg                            40

<210> SEQ ID NO 93
<211> LENGTH: 21
<212> TYPE: DNA
<213> ORGANISM: Artificial Sequence
<220> FEATURE:

<223> OTHER INFORMATION: Primer

<400> SEQUENCE: 93
tgccttcttt acactgacac a                                         21

<210> SEQ ID NO 94
<211> LENGTH: 22
<212> TYPE: DNA
<213> ORGANISM: Artificial Sequence
<220> FEATURE:
<223> OTHER INFORMATION: Primer

<400> SEQUENCE: 94
agtcagtaat tgtacgtcct gg                                        22

<210> SEQ ID NO 95
<211> LENGTH: 44
<212> TYPE: DNA
<213> ORGANISM: Artificial Sequence
<220> FEATURE:
<223> OTHER INFORMATION: Primer

<400> SEQUENCE: 95
atgagtagac ggtccttcgg aaattcatat gtctcagcat ctgg                44

<210> SEQ ID NO 96
<211> LENGTH: 39
<212> TYPE: DNA
<213> ORGANISM: Artificial Sequence
<220> FEATURE:
<223> OTHER INFORMATION: Primer

<400> SEQUENCE: 96
gttagcccag cctgctatga ggatccgtaa cagcatccg                      39

<210> SEQ ID NO 97
<211> LENGTH: 18
<212> TYPE: DNA
<213> ORGANISM: Artificial Sequence
<220> FEATURE:
<223> OTHER INFORMATION: Primer

<400> SEQUENCE: 97
caggagcaag gacagacc                                             18

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
gacatgggca acaatacagc                                           20

<210> SEQ ID NO 99
<211> LENGTH: 42
<212> TYPE: DNA
<213> ORGANISM: Artificial Sequence
<220> FEATURE:
<223> OTHER INFORMATION: Primer

<400> SEQUENCE: 99
gttctcctgg cagtgagaag gttgatggac ctctgaatct ct                  42

```
<210> SEQ ID NO 100
<211> LENGTH: 41
<212> TYPE: DNA
<213> ORGANISM: Artificial Sequence
<220> FEATURE:
<223> OTHER INFORMATION: Primer

<400> SEQUENCE: 100
acgtgtgaag gtattcaagg caatgtggtc aaggagcatt g            41

<210> SEQ ID NO 101
<211> LENGTH: 18
<212> TYPE: DNA
<213> ORGANISM: Artificial Sequence
<220> FEATURE:
<223> OTHER INFORMATION: Primer

<400> SEQUENCE: 101
ccagccatct gtgtctcc                                      18

<210> SEQ ID NO 102
<211> LENGTH: 20
<212> TYPE: DNA
<213> ORGANISM: Artificial Sequence
<220> FEATURE:
<223> OTHER INFORMATION: Primer

<400> SEQUENCE: 102
cattgctgtt tcctgttggg                                    20

<210> SEQ ID NO 103
<211> LENGTH: 41
<212> TYPE: DNA
<213> ORGANISM: Artificial Sequence
<220> FEATURE:
<223> OTHER INFORMATION: Primer

<400> SEQUENCE: 103
acaatggctc acagattcct ggaagccaca gcctctaatt g            41

<210> SEQ ID NO 104
<211> LENGTH: 41
<212> TYPE: DNA
<213> ORGANISM: Artificial Sequence
<220> FEATURE:
<223> OTHER INFORMATION: Primer

<400> SEQUENCE: 104
tcatctggct gtgaaagtga ggcttctctg aggactcctg t            41

<210> SEQ ID NO 105
<211> LENGTH: 22
<212> TYPE: DNA
<213> ORGANISM: Artificial Sequence
<220> FEATURE:
<223> OTHER INFORMATION: Primer

<400> SEQUENCE: 105
tctggtaaga gtctctgact gt                                 22

<210> SEQ ID NO 106
<211> LENGTH: 21
<212> TYPE: DNA
<213> ORGANISM: Artificial Sequence
<220> FEATURE:
<223> OTHER INFORMATION: Primer
```

<400> SEQUENCE: 106
accacaacag gtaggtattg g                                              21

<210> SEQ ID NO 107
<211> LENGTH: 40
<212> TYPE: DNA
<213> ORGANISM: Artificial Sequence
<220> FEATURE:
<223> OTHER INFORMATION: Primer

<400> SEQUENCE: 107
tccagctcgg tcaacatgat gcctgcatgt ctcttgtcag                          40

<210> SEQ ID NO 108
<211> LENGTH: 43
<212> TYPE: DNA
<213> ORGANISM: Artificial Sequence
<220> FEATURE:
<223> OTHER INFORMATION: Primer

<400> SEQUENCE: 108
acgtctacca caagtactcc ctcaatttct tcaggtcatc cct                      43

<210> SEQ ID NO 109
<211> LENGTH: 21
<212> TYPE: DNA
<213> ORGANISM: Artificial Sequence
<220> FEATURE:
<223> OTHER INFORMATION: Primer

<400> SEQUENCE: 109
caccaggtct tctgaaagac a                                              21

<210> SEQ ID NO 110
<211> LENGTH: 20
<212> TYPE: DNA
<213> ORGANISM: Artificial Sequence
<220> FEATURE:
<223> OTHER INFORMATION: Primer

<400> SEQUENCE: 110
gggaatttcc atgccgtcta                                                20

<210> SEQ ID NO 111
<211> LENGTH: 38
<212> TYPE: DNA
<213> ORGANISM: Artificial Sequence
<220> FEATURE:
<223> OTHER INFORMATION: Primer

<400> SEQUENCE: 111
aagcatggaa ctggcggtag tcgtcatcga ggtgaaga                            38

<210> SEQ ID NO 112
<211> LENGTH: 37
<212> TYPE: DNA
<213> ORGANISM: Artificial Sequence
<220> FEATURE:
<223> OTHER INFORMATION: Primer

<400> SEQUENCE: 112
gccagacagc aagagcagtc tcctgtttca cacccac                             37

<210> SEQ ID NO 113
<211> LENGTH: 20

<212> TYPE: DNA
<213> ORGANISM: Artificial Sequence
<220> FEATURE:
<223> OTHER INFORMATION: Primer

<400> SEQUENCE: 113
gcggtagatg aggtacttgg                                              20

<210> SEQ ID NO 114
<211> LENGTH: 18
<212> TYPE: DNA
<213> ORGANISM: Artificial Sequence
<220> FEATURE:
<223> OTHER INFORMATION: Primer

<400> SEQUENCE: 114
cacactccca gccaaagt                                                18

<210> SEQ ID NO 115
<211> LENGTH: 41
<212> TYPE: DNA
<213> ORGANISM: Artificial Sequence
<220> FEATURE:
<223> OTHER INFORMATION: Primer

<400> SEQUENCE: 115
tcagtcagtt tcaggagtcc ctatgtgtcc agagacatcc t                      41

<210> SEQ ID NO 116
<211> LENGTH: 43
<212> TYPE: DNA
<213> ORGANISM: Artificial Sequence
<220> FEATURE:
<223> OTHER INFORMATION: Primer

<400> SEQUENCE: 116
agcagtctga gcttctaccg agttccattg gtagtctcca tag                    43

<210> SEQ ID NO 117
<211> LENGTH: 19
<212> TYPE: DNA
<213> ORGANISM: Artificial Sequence
<220> FEATURE:
<223> OTHER INFORMATION: Primer

<400> SEQUENCE: 117
cacactaagg ctcctccac                                               19

<210> SEQ ID NO 118
<211> LENGTH: 19
<212> TYPE: DNA
<213> ORGANISM: Artificial Sequence
<220> FEATURE:
<223> OTHER INFORMATION: Primer

<400> SEQUENCE: 118
cccacctcaa tccctgttg                                               19

<210> SEQ ID NO 119
<211> LENGTH: 38
<212> TYPE: DNA
<213> ORGANISM: Artificial Sequence
<220> FEATURE:
<223> OTHER INFORMATION: Primer

<400> SEQUENCE: 119
agcgcaatgg ctaccagggc ctggatgcta atcaagat        38

<210> SEQ ID NO 120
<211> LENGTH: 41
<212> TYPE: DNA
<213> ORGANISM: Artificial Sequence
<220> FEATURE:
<223> OTHER INFORMATION: Primer

<400> SEQUENCE: 120
cccattacca cacccacaaa gatcattgag gacattgctg g        41

<210> SEQ ID NO 121
<211> LENGTH: 22
<212> TYPE: DNA
<213> ORGANISM: Artificial Sequence
<220> FEATURE:
<223> OTHER INFORMATION: Primer

<400> SEQUENCE: 121
attcttgaaa gtcgacctgt tc        22

<210> SEQ ID NO 122
<211> LENGTH: 21
<212> TYPE: DNA
<213> ORGANISM: Artificial Sequence
<220> FEATURE:
<223> OTHER INFORMATION: Primer

<400> SEQUENCE: 122
taggtagctc tctgaaggct t        21

<210> SEQ ID NO 123
<211> LENGTH: 38
<212> TYPE: DNA
<213> ORGANISM: Artificial Sequence
<220> FEATURE:
<223> OTHER INFORMATION: Primer

<400> SEQUENCE: 123
ttcctgctcc tcctgtgagt aagaactgct cagccatg        38

<210> SEQ ID NO 124
<211> LENGTH: 42
<212> TYPE: DNA
<213> ORGANISM: Artificial Sequence
<220> FEATURE:
<223> OTHER INFORMATION: Primer

<400> SEQUENCE: 124
ggactgtcag accaggttgt cctcagagac tttgtcaaag gt        42

<210> SEQ ID NO 125
<211> LENGTH: 19
<212> TYPE: DNA
<213> ORGANISM: Artificial Sequence
<220> FEATURE:
<223> OTHER INFORMATION: Primer

<400> SEQUENCE: 125
gataaccacc aggtgagcc        19

<210> SEQ ID NO 126
<211> LENGTH: 18
<212> TYPE: DNA
<213> ORGANISM: Artificial Sequence

```
<220> FEATURE:
<223> OTHER INFORMATION: Primer

<400> SEQUENCE: 126
gagggtcagt ggcaatgg                                                    18

<210> SEQ ID NO 127
<211> LENGTH: 40
<212> TYPE: DNA
<213> ORGANISM: Artificial Sequence
<220> FEATURE:
<223> OTHER INFORMATION: Primer

<400> SEQUENCE: 127
ccttctcctc gtggatcttg ccatccttgg cactcatctc                            40

<210> SEQ ID NO 128
<211> LENGTH: 42
<212> TYPE: DNA
<213> ORGANISM: Artificial Sequence
<220> FEATURE:
<223> OTHER INFORMATION: Primer

<400> SEQUENCE: 128
aacaccacat aacgtgtcct ggttctggaa gcatgtgatg ag                         42

<210> SEQ ID NO 129
<211> LENGTH: 18
<212> TYPE: DNA
<213> ORGANISM: Artificial Sequence
<220> FEATURE:
<223> OTHER INFORMATION: Primer

<400> SEQUENCE: 129
tgcctccagg ttctcaga                                                    18

<210> SEQ ID NO 130
<211> LENGTH: 21
<212> TYPE: DNA
<213> ORGANISM: Artificial Sequence
<220> FEATURE:
<223> OTHER INFORMATION: Primer

<400> SEQUENCE: 130
ggctccatct tcattacgga a                                                21

<210> SEQ ID NO 131
<211> LENGTH: 41
<212> TYPE: DNA
<213> ORGANISM: Artificial Sequence
<220> FEATURE:
<223> OTHER INFORMATION: Primer

<400> SEQUENCE: 131
ccttagcttc tgcgtaggtg agatatggct tgaacgagca g                          41

<210> SEQ ID NO 132
<211> LENGTH: 36
<212> TYPE: DNA
<213> ORGANISM: Artificial Sequence
<220> FEATURE:
<223> OTHER INFORMATION: Primer

<400> SEQUENCE: 132
ttgaaggcgg ccatctcgca gcagcacaga catgaa                                36
```

<210> SEQ ID NO 133
<211> LENGTH: 18
<212> TYPE: DNA
<213> ORGANISM: Artificial Sequence
<220> FEATURE:
<223> OTHER INFORMATION: Primer

<400> SEQUENCE: 133
ccagaccgtg cttctctg                                                 18

<210> SEQ ID NO 134
<211> LENGTH: 20
<212> TYPE: DNA
<213> ORGANISM: Artificial Sequence
<220> FEATURE:
<223> OTHER INFORMATION: Primer

<400> SEQUENCE: 134
acttacaagc agctagaggc                                               20

<210> SEQ ID NO 135
<211> LENGTH: 39
<212> TYPE: DNA
<213> ORGANISM: Artificial Sequence
<220> FEATURE:
<223> OTHER INFORMATION: Primer

<400> SEQUENCE: 135
ccaagcgtct gatccttgct tctacaggca ctggattga                          39

<210> SEQ ID NO 136
<211> LENGTH: 42
<212> TYPE: DNA
<213> ORGANISM: Artificial Sequence
<220> FEATURE:
<223> OTHER INFORMATION: Primer

<400> SEQUENCE: 136
ttccaagtga ggccacttca tccatcagga aataggctca gg                      42

<210> SEQ ID NO 137
<211> LENGTH: 19
<212> TYPE: DNA
<213> ORGANISM: Artificial Sequence
<220> FEATURE:
<223> OTHER INFORMATION: Primer

<400> SEQUENCE: 137
ccggtacagc agcactatt                                                19

<210> SEQ ID NO 138
<211> LENGTH: 21
<212> TYPE: DNA
<213> ORGANISM: Artificial Sequence
<220> FEATURE:
<223> OTHER INFORMATION: Primer

<400> SEQUENCE: 138
tctgagtgaa gaacacttgg c                                             21

<210> SEQ ID NO 139
<211> LENGTH: 37
<212> TYPE: DNA
<213> ORGANISM: Artificial Sequence
<220> FEATURE:
<223> OTHER INFORMATION: Primer

<400> SEQUENCE: 139
acctcggcca atgaacggac atctccaacc tcacaga                                37

<210> SEQ ID NO 140
<211> LENGTH: 39
<212> TYPE: DNA
<213> ORGANISM: Artificial Sequence
<220> FEATURE:
<223> OTHER INFORMATION: Primer

<400> SEQUENCE: 140
atagagtggg aggtgggagc tcttcctcta gcacagacc                              39

<210> SEQ ID NO 141
<211> LENGTH: 22
<212> TYPE: DNA
<213> ORGANISM: Artificial Sequence
<220> FEATURE:
<223> OTHER INFORMATION: Primer

<400> SEQUENCE: 141
gtactgatca cttcctgtcc tc                                                22

<210> SEQ ID NO 142
<211> LENGTH: 18
<212> TYPE: DNA
<213> ORGANISM: Artificial Sequence
<220> FEATURE:
<223> OTHER INFORMATION: Primer

<400> SEQUENCE: 142
cctcgtgctg ccttcatt                                                     18

<210> SEQ ID NO 143
<211> LENGTH: 38
<212> TYPE: DNA
<213> ORGANISM: Artificial Sequence
<220> FEATURE:
<223> OTHER INFORMATION: Primer

<400> SEQUENCE: 143
cgcatcatgg tgttcttgcc aagcagatgc agcagatc                               38

<210> SEQ ID NO 144
<211> LENGTH: 39
<212> TYPE: DNA
<213> ORGANISM: Artificial Sequence
<220> FEATURE:
<223> OTHER INFORMATION: Primer

<400> SEQUENCE: 144
ctctggagaa actgctgcct ctcagtgagg tcctccttg                              39

<210> SEQ ID NO 145
<211> LENGTH: 18
<212> TYPE: DNA
<213> ORGANISM: Artificial Sequence
<220> FEATURE:
<223> OTHER INFORMATION: Primer

<400> SEQUENCE: 145
atcagcacca cagccttc                                                     18

<210> SEQ ID NO 146

```
<211> LENGTH: 20
<212> TYPE: DNA
<213> ORGANISM: Artificial Sequence
<220> FEATURE:
<223> OTHER INFORMATION: Primer

<400> SEQUENCE: 146
ggaatgtggg ctttgtgttc                                                    20
```